US00RE37979E

(19) United States
(12) Reissued Patent
Miyasaka et al.

(10) Patent Number: US RE37,979 E
(45) Date of Reissued Patent: Feb. 4, 2003

(54) PYRIMIDINE DERIVATIVES AND ANTI-VIRAL AGENT CONTAINING THE SAME AS ACTIVE INGREDIENT THEREOF

(75) Inventors: Tadashi Miyasaka, Kanagawa (JP); Hiromichi Tanaka, Kanagawa (JP); Erik Desiré DeClercq, Lovenjoel (BE); Masanori Baba, Kagoshima (JP); Richard Thomas Walker, Birmingham (GB); Masaru Ubasawa, Kanagawa (JP)

(73) Assignee: Mitsubishi Chemical Corporation

(21) Appl. No.: 08/957,358

(22) Filed: Oct. 23, 1997

Related U.S. Patent Documents

Reissue of:
(64) Patent No.: 5,461,060
Issued: Oct. 24, 1995
Appl. No.: 08/222,071
Filed: Sep. 3, 1993

U.S. Applications:

(63) Continuation of application No. 07/590,475, filed on Sep. 28, 1990, now abandoned.

(30) Foreign Application Priority Data

Sep. 29, 1989 (JP) ..... 1-254531
Mar. 9, 1990 (JP) ..... 2-59700
Jul. 27, 1990 (JP) ..... 2-200595

(51) Int. Cl.[7] ..... A61K 31/505; A61P 31/18; C07D 239/02

(52) U.S. Cl. ..... 514/269; 514/274; 544/309; 544/310; 544/311; 544/312; 544/313; 544/314; 544/317

(58) Field of Search ..... 514/269, 274; 544/309, 310, 311, 312, 313, 314, 317

(56) References Cited

U.S. PATENT DOCUMENTS 3,497,515 A * 2/1970 Loux ..... 260/260
4,868,187 A * 9/1989 Ogilvie ..... 544/317
4,897,479 A * 1/1990 Tolman et al. ..... 544/276
4,921,859 A * 5/1990 Sircan et al. ..... 544/276
5,036,071 A * 7/1991 Johansson et al. ..... 544/276
5,043,339 A * 8/1991 Beauchamp ..... 544/276

FOREIGN PATENT DOCUMENTS

DE 2126148 * 12/1972
DE 2142317 * 3/1973
EP 0291230 * 11/1988
EP 03711139 * 6/1990
JP 55-87777 7/1980
WO 8302891 * 9/1983
WO 89/09213 10/1989

OTHER PUBLICATIONS

Tetrahedron Letters, vol. 27, No. 1, Jan., 1986 pp. 113–116.*
Tetrahedron, vol. 39, No. 23, Dec. 1983, pp. 3919–3921.*
Journal of Heterocyclic Chemistry, vol. 19, No. 2 Mar.–Apr. 1982, pp. 301–304.*
Journal of Medicinal Chemistry, vol. 10, No. 3, May 1967, pp. 304–311.*
Journal of Medicinal Chemistry, vol. 10, No. 3, May 1967, pp. 316–320.*
Journal of Medicinal Chemistry, vol. 19, No. 1, Jan. 1976, pp. 71–98.*
Chemical Abstracts, vol. 111, No. 17, 23rd Oct., 1989 p. 728.*
Chemical Abstracts, vol. 106, No. 3, 19th Jan., 1987 p. 613.*
Chem.Parm Bull., 31 (10), 3496–502 (1983).*
J. Chem. Soc. Perkin Trans. 1,12,3114–17 (1981).*
J. Heterocycl. Chem.,18(7), 1329–34 (1981).*
J. Med. Chem., 32(1), 73–6 (1989).*
Tetrahedron Lett., 29(32), 4013–16 (1988).*
J. Med. Chem., 32(12), 2507–9 (1989).*
Bioch. Bioph. Res.Comm., 165(3), 1375–81 (1989).*
U.S. patent application Ser. No. 07/449,930, filing date Oct. 4, 1989.*
Hiromichi Tanaka et al, CA 114–43451n(1990).*
Miyasaka et al, CA 112–77870x(1989).*
Mansuri et al, Chemtech. 1992, p. 564.*
Connolly et al., Antimicrobial Agents and Chemotherapy 1992, p. 245–254.*
Saunders, Drug Design and Discovery 1992, pp. 255–263.*
Saori et al, J . Med. Chem. 1992, 35, 3792–3802. Merck Standby Statement, Sep. 14, 1993.*
Chemical Abstracts 107:129717w, vol. 107 (1987).
C. Chu et al, "Chemistry and Antiviral Activities of Acyclonucleosides", J. Heterocyclic Chem. 23, 289 (1986).

* cited by examiner

*Primary Examiner*—Brenda Coleman
(74) *Attorney, Agent, or Firm*—Dike, Bronstein, Roberts & Cushman/Edwards & Angell; David G. Conlin

(57) ABSTRACT

The disclosure concerns pyrimidine derivatives represented by the following general formulas [I] and [I'] and having antiviral activity, particularly antiretroviral activity such as anti-HIV activity:

[I]

[I']

and pharmaceutical compositions having antiviral activity and comprising the above-described derivative(s) as an active ingredient.

15 Claims, No Drawings

PYRIMIDINE DERIVATIVES AND ANTI-VIRAL AGENT CONTAINING THE SAME AS ACTIVE INGREDIENT THEREOF

Matter enclosed in heavy brackets [ ] appears in the original patent but forms no part of this reissue specification; matter printed in italics indicates the additions made by reissue.

This is a continuation of application Ser. No. 07/590,475 filed on Sep. 28, 1990, now abandoned.

FIELD OF THE INVENTION

The present invention relates to novel 6-substituted acyclopyrimidine derivatives and antiviral agents containing the derivative as the active ingredients.

BACKGROUND OF THE INVENTION

Infectious diseases caused by human acquired immunodeficiency virus (HIV), which is a type of retrovirus, have recently become a serious social problem. A compound of 3'-deoxy-3'-azidothymidine is known as a nucleoside compound used in the clinical treatment for diseases caused by HIV-infection. However, this compound has side-effects since it also exhibits considerable strong toxicity in the host cells.

Although some 2',3'-dideoxyribonucleosides are known as nucleoside compounds exhibiting an anti-viral activity, it is still necessary to develop a substance possessing a higher activity and lower toxicity to the host cell (Hiroaki Mitsuya, Bodily Defense, Vol. 4, pp.213–223 (1987)).

On the other hand, various acyclonucleoside compounds have been synthesized since Acyclovir (acycloguanosine) was developed as an antiviral substance effective against herpes virus (C. K. Chu and S. J. Culter, J. Heterocyclic Chem., 23, p.289 (1986)). However, no acyclonucleoside compound having a sufficient activity especially against retroviruses has yet been discovered.

We have focussed our attention on 6-substituted acyclopyrimidine nucleoside compounds and have synthesized various novel 6-substituted acyclopyrimidine nucleoside derivatives and screened those compounds to detect effective antiviral agents, especially to the retrovirus, in order to provide antiviral agents exhibiting an effective activity particularly against retroviruses.

Some 6-substituted acyclopyrimidine nucleoside compounds such as 6-fluoro substituted derivatives, 6-alkylamino substituted derivatives (DD-A-232492) and 6-methyl substituted derivatives (C. A. 107, 129717w (1987)) are known; however, the antiviral activity of these compounds has not been described.

As a result of our researches for compounds exhibiting an effective antiviral activity, particularly anti-retroviral activity, we found that specific 6-substituted pyrimidine nucleoside compounds according to the invention satisfy the above demand to achieve the present invention.

SUMMARY OF THE INVENTION

The present invention concerns 6-substituted acyclopyrimidine nucleoside derivatives represented by the following general formula I;

[I]

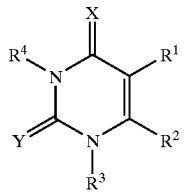

wherein $R^1$ represents a hydrogen atom, halogen atom, alkyl, cycloalkyl, alkenyl, alkynyl, alkylcarbonyl, arylcarbonyl, arylcarbonylalkyl, arylthio or aralkyl group;

$R^2$ represents an arylthio, alkylthio, cycloalkylthio, arylsulfinyl, alkylsulfinyl, cycloalkylsulfinyl, alkenyl, alkynyl, aralkyl, arylcarbonyl, arylcarbonylalkyl or aryloxy group, those groups optionally substituted by one or more of substituents selected from a halogen atom, alkyl, halogenated alkyl, alkoxy, hydroxyl, nitro, amino, cyano and acyl groups;

$R^3$ represents a hydrogen atom, methyl, branched alkyl or $—CH_2—Z—(CH_2)_n—R^5$ group where $R^5$ represents a hydrogen atom, halogen atom, hydroxyl, heterocyclic carbonyloxy, formyloxy, alkylcarbonyloxy, cycloalkylcarbonyloxy, aralkylcarbonyloxy, arylcarbonyloxy, azido, alkoxycarbonyloxy, N-alkylcarbamoyloxy, N-arylcarbamoyloxy, alkoxy, aralkyloxy, branched alkyl, cycloalkyl or aryl group, the alkoxycarbonyloxy to aryl groups mentioned above as $R^5$ optionally substituted by one or more substituents selected from a halogen atom, aryl, alkyl, alkoxy and halogenated alkyl groups, Z represents an oxygen, sulfur atom or methylene group, and n represents 0 or an integer of 1 to 5, $R^4$ represents a hydrogen atom, alkyl or aralkyl group, X and Y represent an oxygen or sulfur atom independently, provided that when $R^4$ and Z represent a hydrogen atom and oxygen atom respectively $R^5$ does not represent a hydroxyl group, or the following general formula I';

[I']

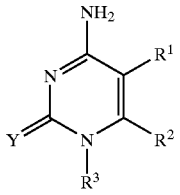

wherein $R^1$, $R^2$, $R^3$ and Y have the same meanings as defined for the formula I above, pharmaceutically acceptable salts thereof and antiviral agents containing the derivative or the salt thereof as an active ingredient.

DETAILED DESCRIPTION OF THE INVENTION

The 6-substituted acyclopyrimidine nucleoside derivatives according to the invention are represented by the general formula I or I'.

The group of $R^1$ represents a hydrogen atom; halogen atom such as chlorine, iodine, bromine and fluorine; alkyl group such as methyl, ethyl, n-propyl, i-propyl and n-butyl; cycloalkyl group such as cyclopropyl, cyclobutyl, cyclopentyl, cyclohexyl and cycloheptyl; alkenyl group such as vinyl, propenyl, butenyl, phenylvinyl, bromovinyl, cyanovinyl, alkoxycarbonylvinyl and carbamoylvinyl; alkynyl group such as ethynyl, propynyl and phenylethynyl; alkylcarbonyl group such as acetyl, propionyl, and i-butyryl; arylcarbonyl group such as benzoyl and naphthoyl; arylcarbonylalkyl group such as phenacyl; arylthio group such as phenylthio, tolylthio and naphthylthio; or aralkyl group such as benzyl.

The group of $R^2$ represents an arylthio group such as phenylthio and naphthylthio; alkylthio group such as methylthio, ethylthio, propylthio, butylthio and pentylthio; cycloalkylthio group such as cyclopentylthio, cyclohexylthio and cycloheptylthio; arylsulfinyl group such as phenylsulfinyl; alkylsulfinyl group such as methylsulfinyl, ethylsulfinyl and butylsulfinyl; cycloalkylsulfinyl group such as cyclopentylsulfinyl and cyclohexylsulfinyl; alkenyl group such as vinyl, propenyl and phenylvinyl; alkynyl group such as ethynyl, propynyl and phenylethynyl; aralkyl group such as benzyl; arylcarbonyl group such as benzoyl; arylcarbonylalkyl group such as phenacyl; or aryloxy group such as phenoxy, and those groups may be optionally substituted by one or more of substituents selected from a halogen atom such as chlorine, bromine, fluorine and iodine, alkyl group such as methyl, ethyl, propyl, butyl and pentyl, a halogenated alkyl group such as trifluoromethyl, alkoxy group such as methoxy, ethoxy, propoxy and butoxy, hydroxyl group, nitro group, amino group, cyano group and acyl group such as acetyl.

The group of $R^3$ represents a hydrogen atom, methyl group, branched alkyl group such as i-propyl and t-butyl or $—CH_2—Z—(CH_2)_n—R^5$ group where $R^5$ represents a hydrogen atom; halogen atom such as fluorine, chlorine, iodine and bromine; hydroxyl group; heterocyclic carbonyloxy group such as nicotinoyloxy; formyloxy group; optionally branched alkylcarbonyloxy group such as acetoxy, propyonyloxy, n-butyryloxy, i-butyryloxy, valeryloxy, hexanoyloxy, heptanoyloxy and decanoyloxy; cycloalkylcarbonyloxy group such as cyclohexylcarbonyloxy; aralkylcarbonyloxy group such as benzylcarbonyloxy; arylcarbonyloxy group such as benzoyloxy, toluoylcarbonyloxy and naphthoylcarbonyloxy group; azido group; alkoxycarbonyloxy group such as methoxycarbonyloxy, ethoxycarbonyloxy, n-propoxycarbonyloxy, i-propoxycarbonyloxy, n-butoxycarbonyloxy and t-butoxycarbonyloxy group, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; N-alkylcarbamoyloxy group such as N-methylcarbamoyloxy, N-ethylcarbamoyloxy, N-propylcarbamoyloxy, N-butylcarbamoyloxy and N-pentylcarbamoyloxy, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; N-arylcarbamoyloxy group such as N-phenylcarbamoyloxy and N-tolylcarbamoyloxy, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; N-alkylthiocarbamoyloxy group such as N-methytiocarbamoyloxy, N-ethylthiocarbamoyloxy, N-propylthiocarbamoyloxy, N-butylthiocarbamoyloxy and N-pentylthiocarbamoyloxy, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; N-arylthiocarbamoyloxy group such as N-phenylthiocarbamoyloxy and N-tolylthiocarbamoyloxy, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; alkoxy group such as methoxy, ethoxy, n-propoxy, i-propoxy, n-butoxy, t-butoxy, n-pentyloxy and n-hexyloxy group, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; branched alkyl group such as i-propyl, i-butyl, sec-butyl, t-butyl, i-heptyl and i-hexyl, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; cycloalkyl group such as cyclopropyl, cyclobutyl, cyclopentyl, cyclohexyl and cycloheptyl, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, alkoxy group such as methoxy, ethoxy, n-propoxy, i-propoxy, n-butoxy and t-butoxy and halogenated alkyl group such as trifluoromethyl; or aryl group such as phenyl, optionally substituted by one or more substituents selected from a halogen atom such as fluorine, chlorine, bromine and iodine, aryl group such as phenyl, toluyl and naphthyl, alkyl group such as methyl, ethyl, n-propyl, i-propyl, n-butyl and t-butyl, an alkoxy group such as methoxy, ethoxy, n-propoxy, i-propoxy, n-butoxy and t-butoxy and halogenated alkyl group such as trifluoromethyl, and Z represents an oxygen, sulfur atom or methylene group, and n represents 0 or an integer of 1 to 5, $R^4$ represents a hydrogen atom; optionally branched alkyl group such as methyl, ethyl, n-propyl, i-propyl, n-butyl and t-butyl; or aralkyl group such as benzyl.

X and Y represent oxygen or sulfur atom independently.

In the above formula I, when $R^4$ and Z represent a hydrogen atom and oxygen atom respectively, $R^5$ does not represent a hydroxyl group.

The preferred compounds according to the invention have $R^1$ of a hydrogen atom, halogen atom, $C_1$ to $C_5$ alkyl group or $C_2$ to $C_5$ alkenyl group, particularly $C_1$ to $C_5$ alkyl group; $R^2$ of $C_6$ to $C_{10}$ arylthio group, $C_3$ to $C_{10}$ cycloalkylthio group or $C_7$ to $C_{11}$ aralkyl group, particularly $C_6$ to $C_{10}$ arylthio, $C_3$ to $C_{10}$ cycloalkylthio or $C_7$ to $C_{11}$ aralkyl group, optionally substituted by one or more substituents selected from a halogen atom, $C_1$ to $C_5$ alkyl, $C_1$ to $C_5$ alkoxy and nitro groups; $R^3$ of a hydrogen atom, methyl or —$CH_2$—Z—$(CH_2)_n$—$R^5$ group where $R^5$ represents a hydrogen atom, halogen atom, hydroxyl, heterocyclic carbonyloxy, $C_2$ to $C_{11}$ alkylcarbonyloxy, $C_4$ to $C_{10}$ cycloalkylcarbonyloxy, $C_8$ to $C_{12}$ aralkylcarbonyloxy, $C_7$ to $C_{13}$ arylcarbonyloxy, $C_2$ to $C_{11}$ alkoxycarbonyloxy, $C_8$ to $C_{10}$ aralkyloxycarbonyloxy, $C_2$ to $C_8$ N-alkylcarbamoyloxy, $C_7$ to $C_{13}$ arylcarbamoyloxy, $C_2$ to $C_8$ alkylthiocarbamoyloxy, $C_7$ to $C_{13}$ arylthiocarbamoyloxy, $C_1$ to $C_{10}$ alkoxy, $C_7$ to $C_{13}$ aralkyloxy, azido, $C_3$ to $C_5$ branched alkyl, $C_5$ to $C_7$ cycloalkyl or $C_6$ to $C_{10}$ aryl group optionally substituted by one or more substituents selected from a halogen atom, aryl, alkyl, alkoxy and halogenated alkyl groups, Z represents an oxygen, sulfur atom or methylene group, and n represents 0 or an integer of 1 to 5; $R^4$ of a hydrogen atom, $C_1$ to $C_{13}$ alkyl or $C_7$ to $C_{11}$ aralkyl group; X of an oxygen or sulfur atom; and Y of an oxygen or sulfur atom; provided that when $R^4$ and Z represent a hydrogen atom and oxygen atom respectively $R^5$ does not represent hydroxyl group, Examples of the preferred compounds according to the present invention are listed in Table 1 below. t,120

TABLE 1

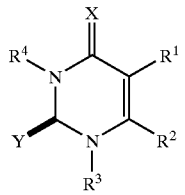

| Compound No. | $R^1$ | $R^2$ | $R^3$ | $R^4$ | X | Y | Melting point (° C.) |
|---|---|---|---|---|---|---|---|
| 1 | —$CH_3$ | 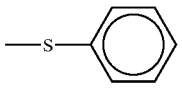 | 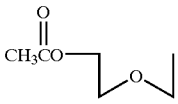 | —H | O | S | 112~113 |
| 2 | " | " | " | " | " | O | 112~113 |
| 3 | " | 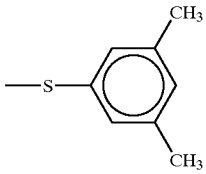 | " | " | " | " | 155.5~156.6 |
| 4 | " | " | " | " | " | S | 144~145 |
| 5 | " | 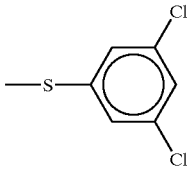 | " | " | " | O | 132~133 |
| 6 | " | 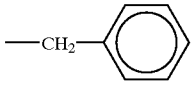 | " | " | " | " | 100~115 |
| 7 | " | 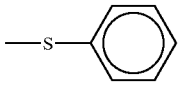 | 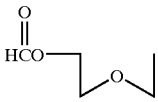 | " | " | " | 120~121 |
| 8 | " | " | 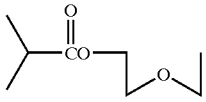 | " | " | " | 107~108 |

TABLE 1-continued
| | | | | | | | |
|---|---|---|---|---|---|---|---|
| 9 | " | " | 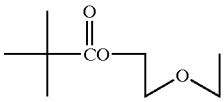 | " | " | " | 9~102 |
| 10 | —$CH_3$ | 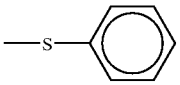 | 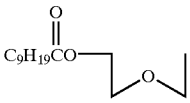 | —H | O | O | 80~81 |
| 11 | " | " | 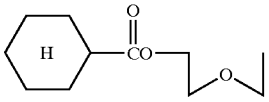 | " | " | " | 101~102 |
| 12 | " | " | 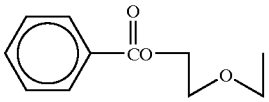 | " | " | " | 132~133 |
| 13 | " | " | 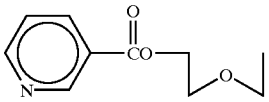 | " | " | " | 139~140 |
| 14 | " | " | 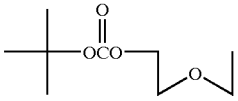 | " | " | " | 115~119 |
| 15 | " | 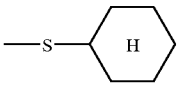 | 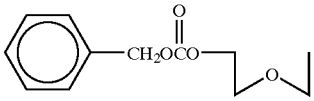 | " | " | " | 95~97 |
| 16 | " | 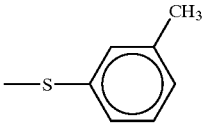 | 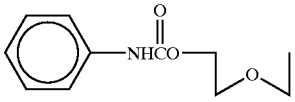 | " | " | " | 175~176 |
| 17 | " | " | 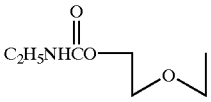 | " | " | " | 148~150 |
| 18 | " | " | 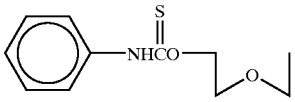 | " | " | " | 157~159 |
| 19 | " | 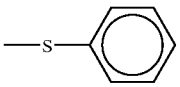 | 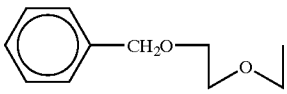 | " | " | " | 107~109 |
| 20 | " | " | 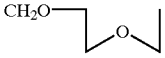 | " | " | " | 102~104 |
| 21 | —$CH_3$ | 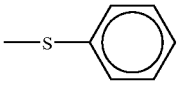 | 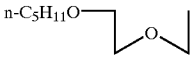 | —H | O | O | 74~80 |
| 22 | " | " | 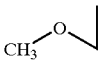 | " | " | " | 148~150 |

TABLE 1-continued

| | | | | | | | |
|---|---|---|---|---|---|---|---|
| 23 | " | " | $CH_3$ O | " | " | " | 133~134 |
| 24 | " | " | $N_2$ O | " | " | " | 91~92 |
| 25 | " | " | F O | " | " | " | 136~137 |
| 26 | " | " | Cl O | " | " | " | 123~124 |
| 27 | " | " | H | " | " | " | 238~242 |
| 28 | " | " | $CH_3$ | " | " | " | 229~230 |
| 29 | " | " | $C_2H_5$ | " | " | " | 158~160 |
| 30 | " | " | $CH_3$ | " | " | " | 124~127 |
| 31 | " | " | HO | " | " | " | 157~158 |
| 32 | —$CH_3$ | —S— | $CH_3$ S | —H | O | O | 159~161 |
| 33 | " | " | HO O | —$CH_2$— | " | " | Oil |
| 34 | " | " | HO O | —$CH_3$ | " | " | 74~75 |
| 35 | " | " | O $CH_2CO$ O | —H | " | " | |
| 36 | " | " | O $C_2H_5NHCO$ O | " | " | " | |
| 37 | " | " | O $CH_3CH_2CH_2NCO$ H O | " | " | " | |
| 38 | " | " | O NH CO O | " | " | " | |
| 39 | " | " | O $CH_2NHCO$ O | " | " | " | |

TABLE 1-continued
| | | | | | | | |
|---|---|---|---|---|---|---|---|
| 40 | " | " | 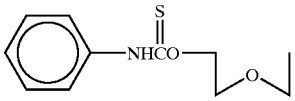 | " | " | " | |
| 41 | " | " | 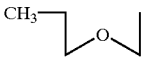 | " | " | " | 136~138 |
| 42 | " | " | 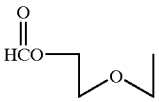 | " | " | S | |
| 43 | —$CH_3$ | 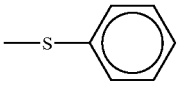 | 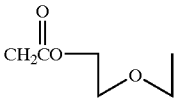 | —$CH_3$ | O | S | |
| 44 | " | " | 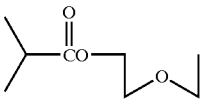 | —H | " | " | |
| 45 | " | " | 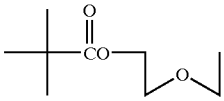 | " | " | " | |
| 46 | " | " | 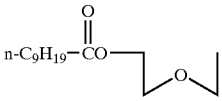 | " | " | " | |
| 47 | " | " | 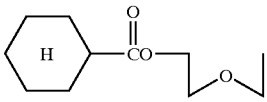 | " | " | " | |
| 48 | " | " | 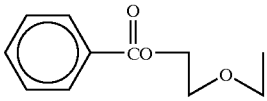 | " | " | " | |
| 49 | " | " | 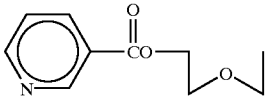 | " | " | " | |
| 50 | " | " | 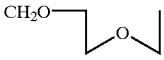 | " | " | " | |
| 51 | " | " | 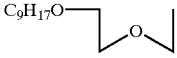 | " | " | " | |
| 52 | " | " | 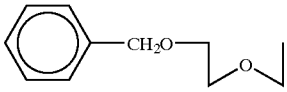 | " | " | " | |
| 53 | " | " | 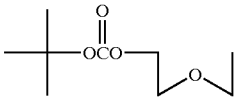 | " | " | " | |

TABLE 1-continued
| | | | | | | |
|---|---|---|---|---|---|---|
| 54 | —$CH_3$ | 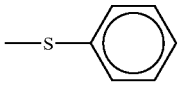 | 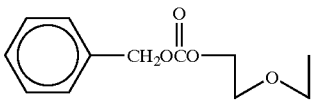 | —H | O | S |
| 55 | " | " | 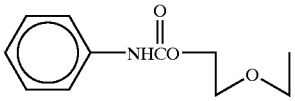 | " | " | " |
| 56 | " | " | 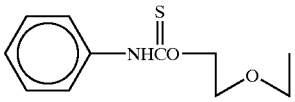 | " | " | " |
| 57 | " | " | 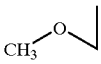 | " | " | " |
| 58 | " | " | 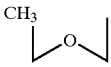 | " | " | " |
| 59 | " | " | 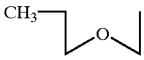 | " | " | " |
| 60 | " | " | 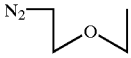 | " | " | " |
| 61 | " | " | 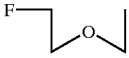 | " | " | " |
| 62 | " | " | 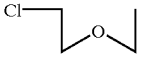 | " | " | " |
| 63 | " | " | 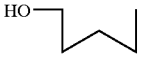 | " | " | " |
| 64 | " | " | 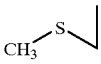 | " | " | " |
| 65 | —$CH_3$ | 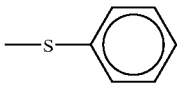 | 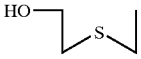 | —H | O | S |
| 66 | " | " | 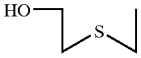 | " | " | O |
| 67 | " | 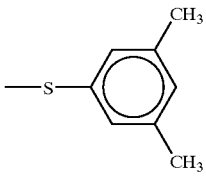 | 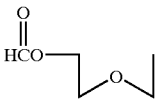 | " | " | " |
| 68 | " | " | 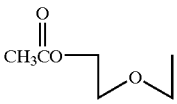 | 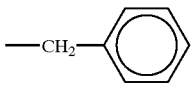 | " | " |
| 69 | " | " | 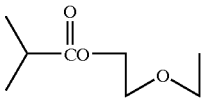 | —H | " | " |

TABLE 1-continued
| | | | | | | |
|---|---|---|---|---|---|---|
| 70 | " | " | 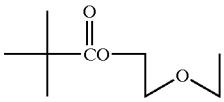 | " | " | " |
| 71 | " | " | 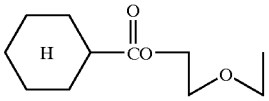 | " | " | " |
| 72 | " | " | 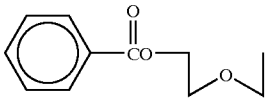 | " | " | " |
| 73 | " | " | 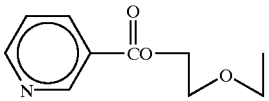 | " | " | " |
| 74 | " | " | 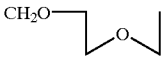 | " | " | " |
| 75 | " | " | 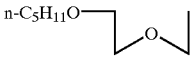 | " | " | " |
| 76 | —$CH_3$ | 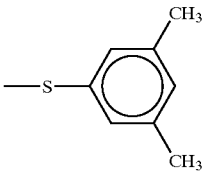 | 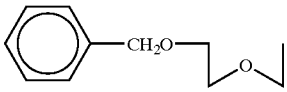 | —H | O | O |
| 77 | " | " | 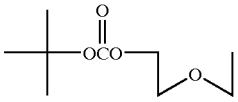 | " | " | " |
| 78 | " | " | 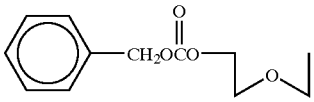 | " | " | " |
| 79 | " | " | 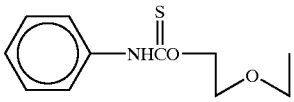 | " | " | " |
| 80 | " | " | 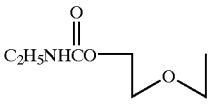 | " | " | " |
| 81 | " | " | 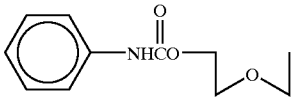 | " | " | " |
| 82 | " | " | 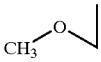 | " | " | " |
| 83 | " | " | 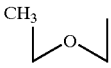 | " | " | " |

TABLE 1-continued

| | | | | | | |
|---|---|---|---|---|---|---|
| 84 | " | " | $CH_3$—O— | " | " | " |
| 85 | " | " | $N_2$—O— | " | " | " |
| 86 | " | " | F—O— | " | " | " |
| 87 | —$CH_3$ | —S—(2,6-$CH_3$) | Cl—O— | —H | O | O |
| 88 | " | " | —H | " | " | " |
| 89 | " | " | —$CH_3$ | " | " | " |
| 90 | " | " | —$C_2H_5$ | " | " | " |
| 91 | " | " | $CH_3$— | " | " | " |
| 92 | " | " | HO—O— | " | " | " |
| 93 | " | " | $CH_3$—S— | " | " | " |
| 94 | " | " | HO—S— | " | " | " |
| 95 | " | —S—(2,6-Cl) | HCO(=O)—O— | " | " | " |
| 96 | " | " | (i-Pr)CO(=O)—O— | " | " | " |
| 97 | " | " | (t-Bu)CO(=O)—O— | " | " | " |
| 98 | —$CH_3$ | —S—(2,6-Cl) | $nC_9H_{19}CO$(=O)—O— | —H | O | O |

TABLE 1-continued
| | | | | | | |
|---|---|---|---|---|---|---|
| 99 | " | " | 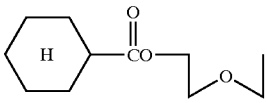 | " | " | " |
| 100 | " | " | 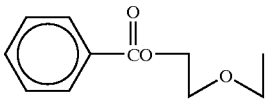 | " | " | " |
| 101 | " | " | 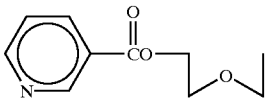 | " | " | " |
| 102 | " | " | 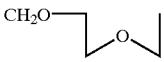 | " | " | " |
| 103 | " | " | 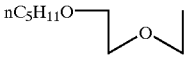 | " | " | " |
| 104 | " | " | 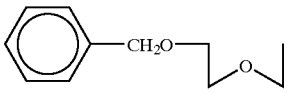 | " | " | " |
| 105 | " | " | 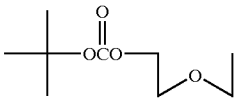 | " | " | " |
| 106 | " | " | 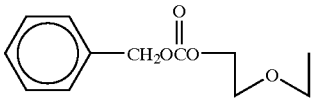 | " | " | " |
| 107 | " | " | 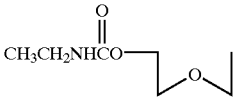 | " | " | " |
| 108 | " | " | 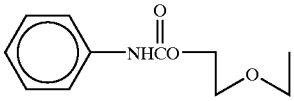 | " | " | " |
| 109 | —$CH_3$ | 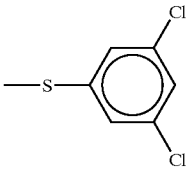 | 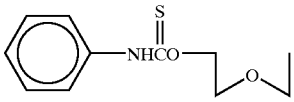 | —H | O | O |
| 110 | " | " | 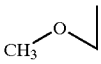 | " | " | " |
| 111 | " | " | 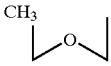 | " | " | " |
| 112 | " | " | 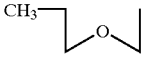 | " | " | " |
| 113 | " | " | 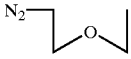 | " | " | " |

TABLE 1-continued
| | | | | | | |
|---|---|---|---|---|---|---|
| 114 | " | " | 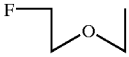 | " | " | " |
| 115 | " | " | 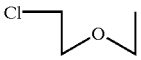 | " | " | " |
| 116 | " | " | 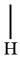 | " | " | " |
| 117 | " | " | 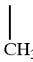 | " | " | " |
| 118 | " | " | 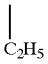 | " | " | " |
| 119 | " | " | 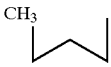 | " | " | " |
| 120 | —$CH_3$ | 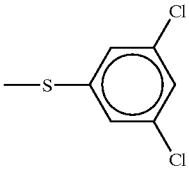 | 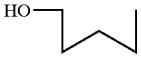 | —H | O | O |
| 121 | " | " | 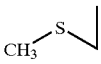 | " | " | " |
| 122 | " | " | 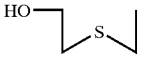 | " | " | " |
| 123 | " | 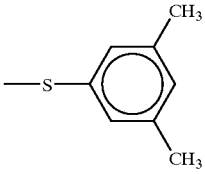 | 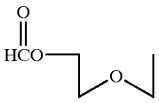 | " | " | S |
| 124 | " | " | 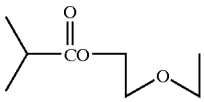 | " | " | " |
| 125 | " | " | 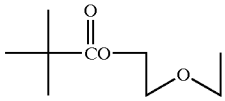 | " | " | " |
| 126 | " | " | 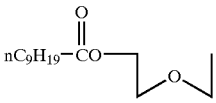 | " | " | " |
| 127 | " | " | 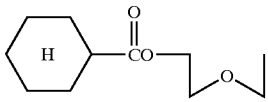 | " | " | " |
| 128 | " | " | 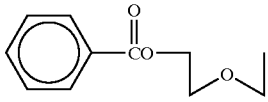 | " | " | " |

TABLE 1-continued
| | | | | | | |
|---|---|---|---|---|---|---|
| 129 | " | " | 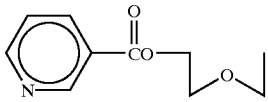 | " | " | " |
| 130 | " | " | 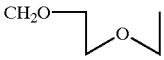 | " | " | " |
| 131 | —$CH_3$ | 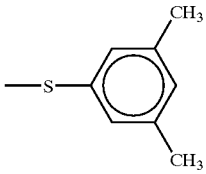 | 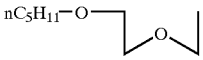 | —H | O | S |
| 132 | " | " | 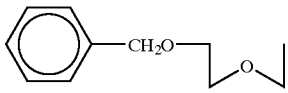 | " | " | " |
| 133 | " | " | 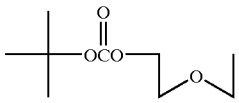 | " | " | " |
| 134 | " | " | 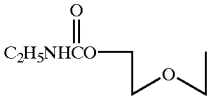 | " | " | " |
| 135 | " | " | 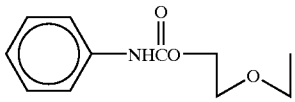 | " | " | " |
| 136 | " | " | 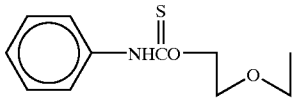 | " | " | " |
| 137 | " | " | 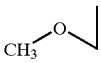 | " | " | " |
| 138 | " | " | 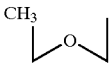 | " | " | " |
| 139 | " | " | 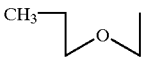 | " | " | " |
| 140 | " | " | 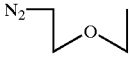 | " | " | " |
| 141 | " | " | 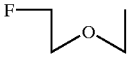 | " | " | " |
| 142 | —$CH_3$ | 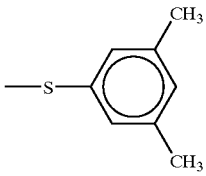 | 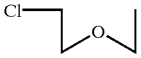 | —H | O | S |

TABLE 1-continued

| | | | | | | |
|---|---|---|---|---|---|---|
| 143 | " | " | H | " | " | " |
| 144 | " | " | $CH_3$ | " | " | " |
| 145 | " | " | $C_2H_5$ | " | " | " |
| 146 | " | " | $CH_3$ | " | " | " |
| 147 | " | " | HO—S | " | " | " |
| 148 | " | " | $CH_3$—S | " | " | " |
| 149 | " | " | HO—S | " | " | " |
| 150 | " | —S—(2,4-Cl) | $CH_3CO$—O | " | " | " |
| 151 | " | " | C6H5—CO—O | " | " | " |
| 152 | " | " | n-$C_9H_{19}$—CO—O | " | " | " |
| 153 | —$CH_3$ | —S—(2,4-Cl) | N—CO—O | —H | O | S |
| 154 | " | " | $CH_2O$—O | " | " | " |
| 155 | " | " | C6H5—$CH_2O$—O | " | " | " |
| 156 | " | " | $CH_3$ | " | " | " |
| 157 | " | " | $CH_2CH_3$ | " | " | " |
| 158 | " | " | $CH_3$ | " | " | " |

TABLE 1-continued

| | | | | | | |
|---|---|---|---|---|---|---|
| 159 | " | " | $CH_3$ | " | " | " |
| 160 | " | " | $CH_3S$ | " | " | " |
| 161 | " | " | HO S | " | " | " |
| 162 | " | " | HO | " | " | " |
| 163 | " | $CH_3$ S | $CH_3CO$ O O | " | " | O |
| 164 | —$CH_3$ | $CH_3$ S | n-$C_9H_{19}$ CO O O | —H | O | O |
| 165 | " | " | CO O O | " | " | " |
| 166 | " | " | CO O O N | " | " | " |
| 167 | " | " | CO O O | " | " | " |
| 168 | " | " | $CH_2O$ O | " | " | " |
| 169 | " | " | $CH_2O$ O | " | " | " |
| 170 | " | " | OCO O O | " | " | " |
| 171 | " | " | $CH_2OCO$ O O | " | " | " |
| 172 | " | " | $CH_3O$ | " | " | " |
| 173 | " | " | $CH_3$ O | " | " | " |
| 174 | " | " | $CH_3$ O | " | " | " |

TABLE 1-continued
| | | | | | | |
|---|---|---|---|---|---|---|
| 175 | —$CH_3$ | 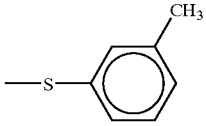 | 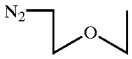 | —H | O | O |
| 176 | " | " | 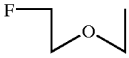 | " | " | " |
| 177 | " | " | 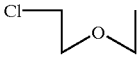 | " | " | " |
| 178 | " | " | 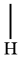 | " | " | " |
| 179 | " | " | 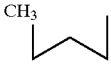 | " | " | " |
| 180 | " | " | 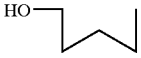 | " | " | " |
| 181 | " | " | 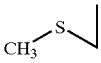 | " | " | " |
| 182 | " | " | 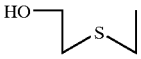 | " | " | " |
| 183 | " | 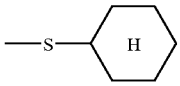 | 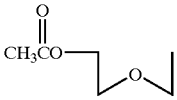 | " | " | " |
| 184 | " | " | 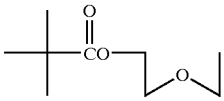 | " | " | " |
| 185 | " | " | 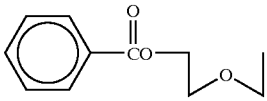 | " | " | " |
| 186 | —CH3 | 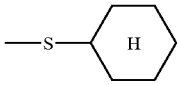 | 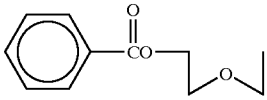 | —H | O | O |
| 187 | " | " | 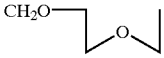 | " | " | " |
| 188 | " | " | 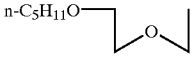 | " | " | " |
| 189 | " | " | 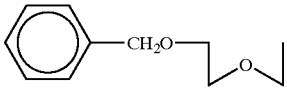 | " | " | " |
| 190 | " | " | 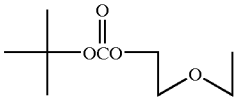 | " | " | " |

TABLE 1-continued
| | | | | | | |
|---|---|---|---|---|---|---|
| 191 | " | " | 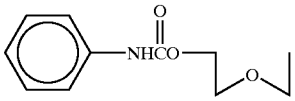 | " | " | " |
| 192 | " | " | 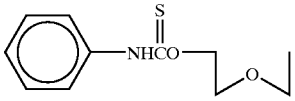 | " | " | " |
| 193 | " | " | 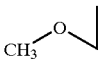 | " | " | " |
| 194 | " | " | 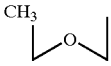 | " | " | " |
| 195 | " | " | 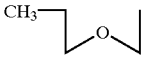 | " | " | " |
| 196 | " | " | 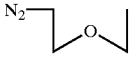 | " | " | " |
| 197 | —$CH_3$ | 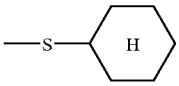 | 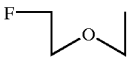 | —H | O | O |
| 198 | " | " | 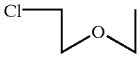 | " | " | " |
| 199 | " | " | 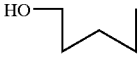 | " | " | " |
| 200 | " | " | 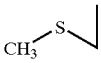 | " | " | " |
| 201 | " | " | 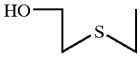 | " | " | " |
| 202 | " | 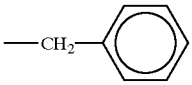 | 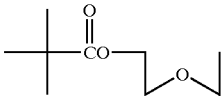 | " | " | " |
| 203 | " | " | 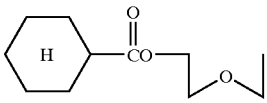 | " | " | " |
| 204 | " | " | 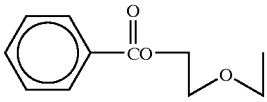 | " | " | " |
| 205 | " | " | 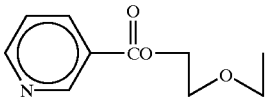 | " | " | " |
| 206 | " | " | 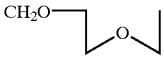 | " | " | " |
| 207 | " | " | 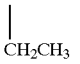 | " | " | " |

TABLE 1-continued
| | | | | | | |
|---|---|---|---|---|---|---|
| 208 | $—CH_3$ | $—CH_2—$ 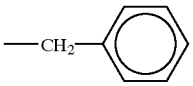 | 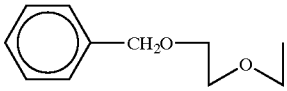 | —H | O | O |
| 209 | " | " | 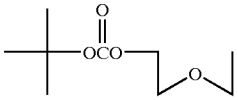 | " | " | " |
| 210 | " | " | 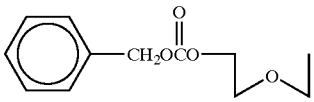 | " | " | " |
| 211 | " | " | 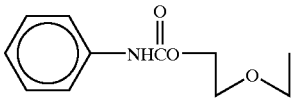 | " | " | " |
| 212 | " | " | 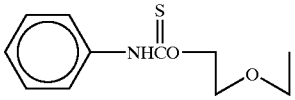 | " | " | " |
| 213 | " | " | 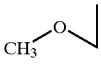 | " | " | " |
| 214 | " | " | 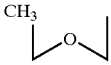 | " | " | " |
| 215 | " | " | 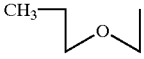 | " | " | " |
| 216 | " | " | 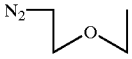 | " | " | " |
| 217 | " | " | 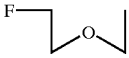 | " | " | " |
| 218 | " | " | 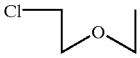 | " | " | " |
| 219 | $—CH_3$ | $—CH_2—$ 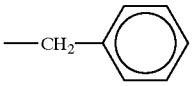 | 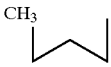 | —H | O | O |
| 220 | " | " | 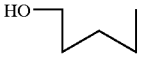 | " | " | " |
| 221 | " | " | 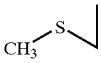 | " | " | " |
| 222 | " | " | 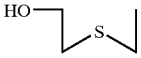 | " | " | " |
| 223 | " | 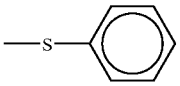 | 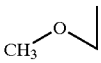 | $—CH_3$ | " | S |
| 224 | " | " | 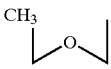 | 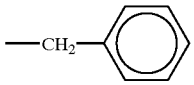 | " | " |

TABLE 1-continued

| | | | | | | |
|---|---|---|---|---|---|---|
| 225 | " | " | $N_2$ O | $—CH_3$ | " | " |
| 226 | " | " | F O | " | " | " |
| 227 | " | " | Cl O | " | " | " |
| 228 | " | " | $CH_2O$ O | " | " | " |
| 229 | " | $CH_3$ S $CH_3$ | $CH_3$ O | " | " | " |
| 230 | $—CH_3$ | $CH_3$ S $CH_3$ | $CH_2O$ O | $—CH_2$ | O | S |
| 231 | " | " | $N_2$ O | " | " | " |
| 232 | " | " | F O | " | " | " |
| 233 | " | " | Cl O | " | " | " |
| 234 | " | " | $CH_2O$ O | $—CH_3$ | " | " |
| 235 | " | " | $CH_3$ O | $—CH_2$ | " | " |
| 236 | $—C_2H_5$ | S | $CH_3CO$ O | —H | " | O |
| 237 | " | " | CO O | " | " | " |
| 238 | " | " | n-$C_9H_{19}$ CO O | " | " | " |
| 239 | " | " | $CH_2O$ O | " | " | " |

TABLE 1-continued
| | | | | | | | |
|---|---|---|---|---|---|---|---|
| 240 | " | " | 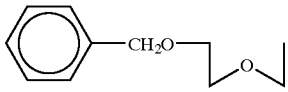 | " | " | " | |
| 241 | $-C_2H_5$ | 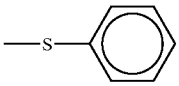 | 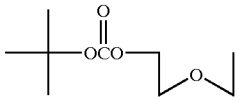 | —H | O | O | |
| 242 | " | " | 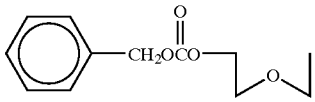 | " | " | " | |
| 243 | " | " | 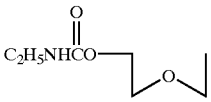 | " | " | " | |
| 244 | " | " | 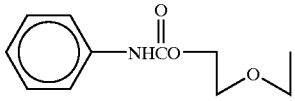 | " | " | " | |
| 245 | " | " | 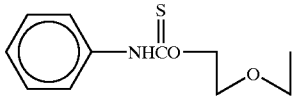 | " | " | " | |
| 246 | " | " | 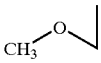 | " | " | " | |
| 247 | " | " | 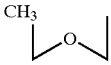 | " | " | " | 123~125 |
| 248 | " | " | 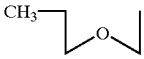 | " | " | " | |
| 249 | " | " | 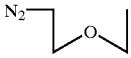 | " | " | " | |
| 250 | " | " | 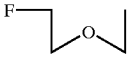 | " | " | " | |
| 251 | " | " | 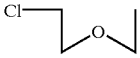 | " | " | " | |
| 252 | $-C_2H_5$ | 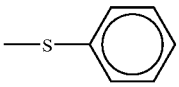 | 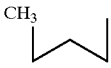 | —H | O | O | 107~108 |
| 253 | " | " | 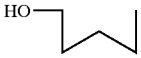 | " | " | " | |
| 254 | " | " | 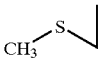 | " | " | " | |
| 255 | " | " | 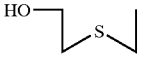 | " | " | " | |
| 256 | " | " | 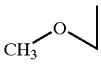 | $-CH_3$ | " | " | |

TABLE 1-continued

| | | | | | | | |
|---|---|---|---|---|---|---|---|
| 257 | " | " | $CH_3O$ | $—CH_2—C_6H_5$ | " | " | |
| 258 | " | " | $CH_3S$ | $—CH_3$ | " | " | |
| 259 | " | " | $CH_3CO(=O)$ S | " | " | " | |
| 260 | " | —S— 2,6-dichlorophenyl | $CH_3O$ | H | " | S | |
| 261 | " | " | $CH_3O$ | " | " | O | |
| 262 | " | " | $CH_3O$ S | $—CH_3$ | " | S | |
| 263 | $—C_2H_5$ | —S— 2,6-dichlorophenyl | $CH_3O$ | —H | O | S | |
| 264 | " | " | $C_6H_5CO(=O)$ | " | " | " | |
| 265 | " | " | F S | $—CH_3$ | " | " | |
| 266 | —CH═CHBr | —S—$C_6H_5$ | $CH_3CO(=O)$ O | H | " | " | |
| 267 | " | " | $CH_2O$ O | " | " | O | |
| 268 | " | " | $C_6H_5NHCO(=O)$ O | " | " | " | |
| 269 | " | " | $CH_3O$ | " | " | " | |
| 270 | " | " | $CH_3$ O | " | " | " | 143~148 |
| 271 | " | " | F O | " | " | S | |

TABLE 1-continued

| | | | | | | |
|---|---|---|---|---|---|---|
| 272 | " | " | HO— | " | " | " |
| 273 | " | " | $CH_3$—S— | " | " | " |
| 274 | —CH═CHBr | —S— | $CH_3O$— —S— | —H | O | S |
| 275 | " | " | $CH_3CO$(=O)— —S— | —$CH_3$ | " | " |
| 276 | " | —S— ($CH_3$, $CH_3$) | $CH_3CO$(=O)— —O— | H | " | O |
| 277 | " | " | $CH_2O$— —O— | " | " | " |
| 278 | —$CH_3$ | —S— | $CH_3O$— —S— | " | " | S |
| 279 | " | " | $CH_3$—O— | " | " | O |
| 280 | " | " | " | —$CH_2$— | " | S |
| 281 | " | " | $CH_3O$— | H | " | " |
| 282 | " | —S— ($CH_3$, $CH_3$) | n-$C_9H_{19}$—CO(=O)— —O— | " | " | O |
| 283 | " | " | $CH_3O$— | " | " | " |
| 284 | " | " | $CH_3O$— —S— | " | " | " |
| 285 | —$CH_3$ | —S— ($CH_3$, $CH_3$) | $CH_3$—O— | —$CH_3$ | O | O |

TABLE 1-continued
| | | | | | | |
|---|---|---|---|---|---|---|
| 286 | " | 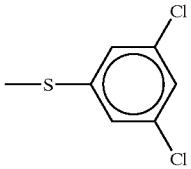 | 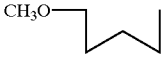 | H | " | " |
| 287 | " | " | 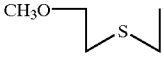 | " | " | " |
| 288 | " | 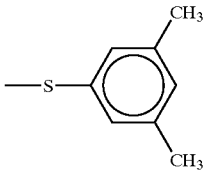 | 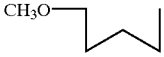 | " | " | S |
| 289 | " | " | 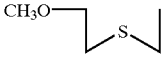 | " | " | " |
| 290 | " | " | 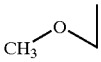 | —$CH_3$ | " | " |
| 291 | " | 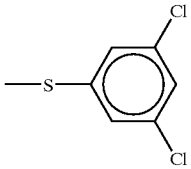 | 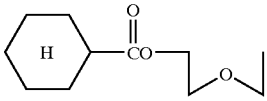 | H | " | " |
| 292 | " | " | 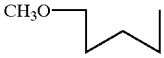 | " | " | " |
| 293 | " | " | 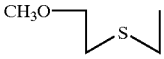 | " | " | " |
| 294 | " | 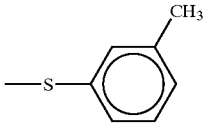 | 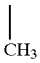 | " | " | O |
| 295 | " | " | 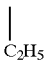 | " | " | " |
| 296 | —$CH_3$ | 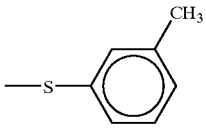 | 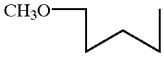 | —H | O | O |
| 297 | " | " | 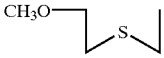 | " | " | " |
| 298 | " | " | 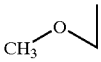 | " | " | S |
| 299 | " | " | 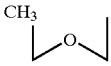 | " | " | " |

TABLE 1-continued
| | | | | | | |
|---|---|---|---|---|---|---|
| 300 | " | 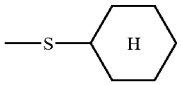 | 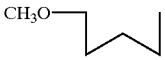 | " | " | " |
| 301 | " | " | 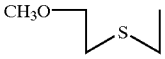 | " | " | " |
| 302 | " | " | 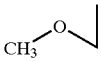 | " | " | " |
| 303 | " | " | 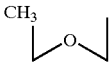 | " | " | " |
| 304 | " | 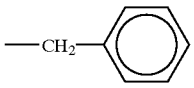 | 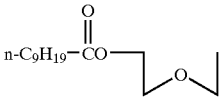 | " | " | O |
| 305 | " | " | 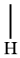 | " | " | " |
| 306 | " | " | 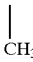 | " | " | " |
| 307 | —$CH_3$ | 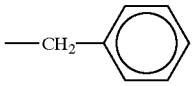 | 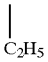 | —H | O | O |
| 308 | " | " | 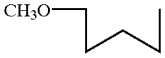 | " | " | " |
| 309 | " | " | 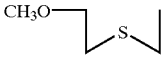 | " | " | " |
| 310 | " | " | 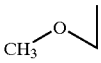 | " | " | S |
| 311 | " | " | 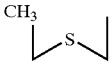 | " | " | " |
| 312 | " | 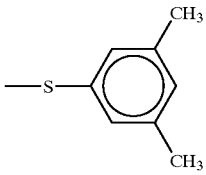 | 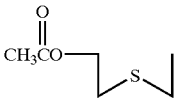 | " | " | " |
| 313 | " | " | 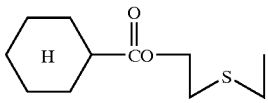 | " | " | " |
| 314 | " | " | 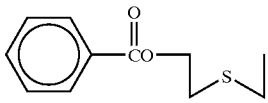 | " | " | " |
| 315 | " | " | 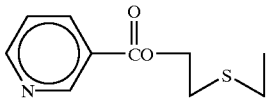 | " | " | " |

TABLE 1-continued
| | | | | | | |
|---|---|---|---|---|---|---|
| 316 | " | " | 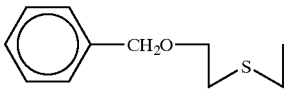 | " | " | " |
| 317 | " | " | 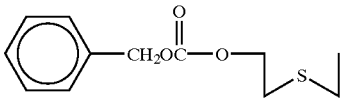 | " | " | " |
| 318 | —$CH_3$ | 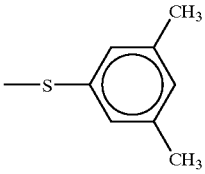 | 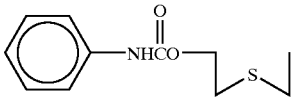 | —H | O | S |
| 319 | " | " | 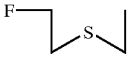 | " | " | " |
| 320 | " | 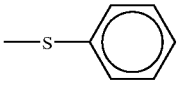 | 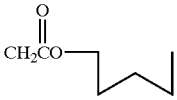 | " | " | " |
| 321 | " | " | 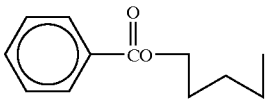 | " | " | " |
| 322 | " | " | 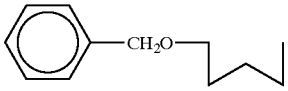 | " | " | " |
| 323 | " | " | 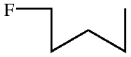 | " | " | " |
| 324 | " | " | 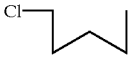 | " | " | " |
| 325 | " | " | 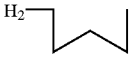 | " | " | " |
| 326 | " | " | 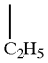 | " | " | " |
| 327 | " | " | 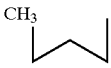 | " | " | " |
| 328 | " | 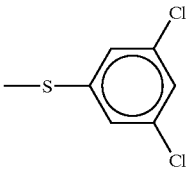 | 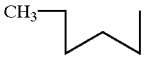 | " | " | O |
| 329 | —$CH_3$ | 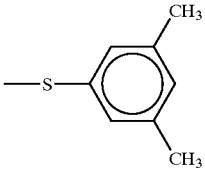 | 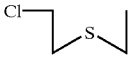 | —H | O | S |

TABLE 1-continued

| | | | | | | |
|---|---|---|---|---|---|---|
| 330 | " | " | $CH_2CO$ | " | " | " |
| 331 | " | " | n-$C_9H_{19}$—CO | " | " | " |
| 332 | " | " | H, CO | " | " | " |
| 333 | " | " | CO | " | " | " |
| 334 | " | " | N, CO | " | " | " |
| 335 | " | " | n-$C_5H_{11}$—O | " | " | " |
| 336 | " | " | CO | " | " | " |
| 337 | " | " | $CH_2OCO$ | " | " | " |
| 338 | " | " | $CH_3CH_2NHCO$ | " | " | " |
| 339 | " | " | NHCO | " | " | " |
| 340 | —$CH_3$ | S, $CH_3$, $CH_3$ | S, NHCO | —H | O | S |
| 341 | " | S | n-$C_5H_{11}$—O, O | " | " | " |
| 342 | " | S, H | H, CO, O | " | " | " |

TABLE 1-continued

| | | | | | | | |
|---|---|---|---|---|---|---|---|
| 343 | " | " | $CH_3$ | " | " | " | |
| 344 | " | " | $C_2H_5$ | " | " | " | |
| 345 | " | " | $CH_3$ | " | " | " | |
| 346 | $—C_2H_5$ | —S— | O, CO, N, O | " | " | " | |
| 347 | " | " | $CH_3$ | " | " | " | |
| 348 | " | " | $C_2H_5$ | " | " | " | |
| 349 | " | " | O, CO, H, O | " | " | " | |
| 350 | " | " | O, n-$C_9H_{19}$—CO, O | " | " | " | |
| 351 | —CH═CHBr | —S— | $C_2H_5$ | —H | O | S | |
| 352 | " | " | $CH_3$ | " | " | " | |
| 353 | " | " | O, CO, O | " | " | " | |
| 354 | " | " | O, $CH_2OCO$, O | " | " | " | |
| 355 | " | " | $CH_3$, O | " | " | " | |
| 356 | " | " | HO, S | " | " | " | |
| 357 | $—C_2H_5$ | —S—, $CH_3$, $CH_3$ | $CH_3$, O | " | " | O | 165~166 |

TABLE 1-continued
| | | | | | | | |
|---|---|---|---|---|---|---|---|
| 358 | " | 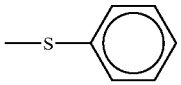 | " | " | " | S | 106~109 |
| 359 | " | 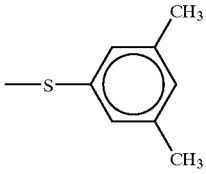 | " | " | " | " | 155~156 |
| 360 | " | 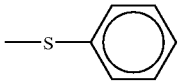 | 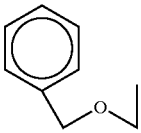 | " | " | O | 110~112 |
| 361 | " | 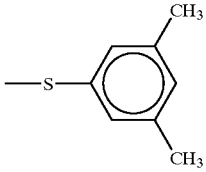 | " | " | " | " | 156~158 |
| 362 | —$CH_3$ | 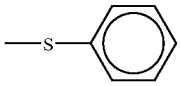 | 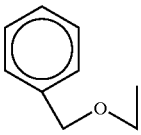 | —H | O | O | 157~161 |
| 363 | —$C_2H_5$ | " | " | " | " | S | 151~153 |
| 364 | " | 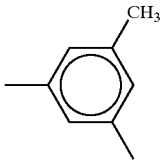 | " | " | " | " | 158~160 |
| 365 | " | 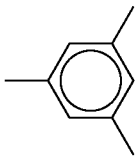 | 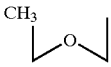 | " | " | O | 159~162 |
| 366 | " | " | " | " | " | S | 112~116 |
| 367 | " | " | 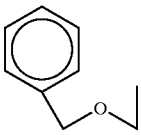 | " | " | O | |
| 368 | " | " | " | " | " | S | |
| 369 | " | 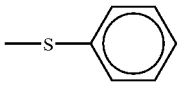 | 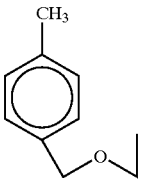 | " | " | O | |

TABLE 1-continued
| | | | | | | | |
|---|---|---|---|---|---|---|---|
| 370 | " | 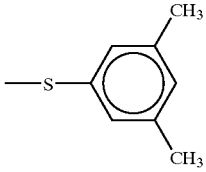 | " | " | " | " | |
| 371 | " | 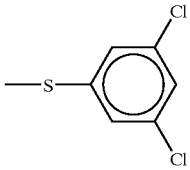 | " | " | " | " | |
| 372 | $—C_2H_5$ | 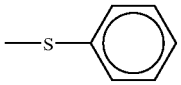 | 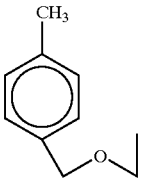 | —H | O | S | 157~160 |
| 373 | " | 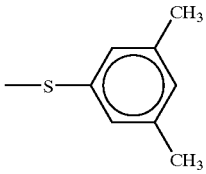 | " | " | " | " | |
| 374 | " | 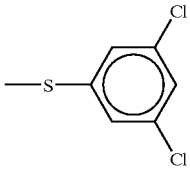 | " | " | " | " | |
| 375 | " | 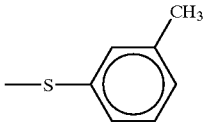 | 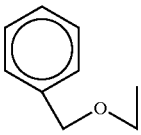 | " | " | O | |
| 376 | " | " | " | " | " | S | |
| 377 | " | " | 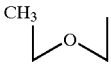 | " | " | O | |
| 378 | " | " | " | " | " | S | |
| 379 | $—CH_3$ | 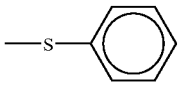 | 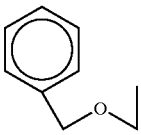 | " | " | " | |
| 380 | " | 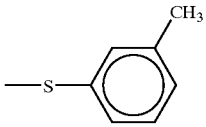 | " | " | " | O | |
| 381 | " | " | " | " | " | S | |

TABLE 1-continued
| | | | | | | |
|---|---|---|---|---|---|---|
| 382 | —$CH_3$ | 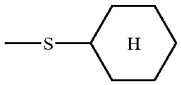 | 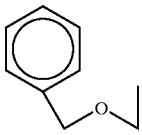 | —H | O | O |
| 383 | " | " | " | " | " | S |
| 384 | " | 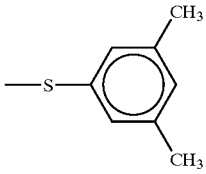 | " | " | " | O |
| 385 | " | " | " | " | " | S |
| 386 | " | 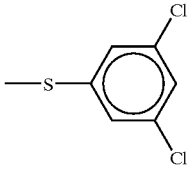 | " | " | " | O |
| 387 | " | " | " | " | " | S |
| 388 | " | 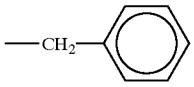 | " | " | " | O |
| 389 | " | " | " | " | " | S |
| 390 | " | 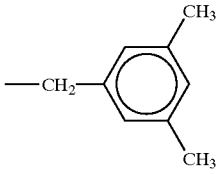 | " | " | " | O |
| 391 | " | " | " | " | " | S |
| 392 | " | 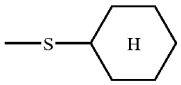 | 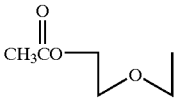 | " | " | " |
| 393 | " | 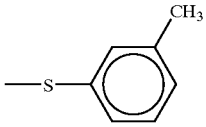 | 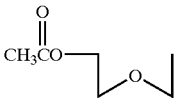 | " | " | " |
| 394 | " | 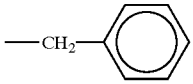 | " | " | " | " |
| 395 | " | 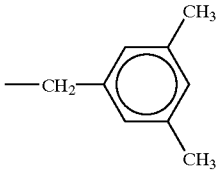 | " | " | " | O |
| 396 | " | " | " | " | " | S |

TABLE 1-continued
| | | | | | | |
|---|---|---|---|---|---|---|
| 397 | " | 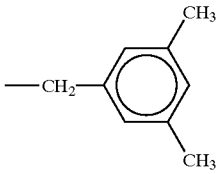 | 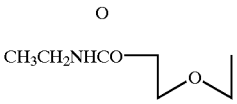 | " | " | " |
| 398 | " | " | " | " | " | O |
| 399 | " | 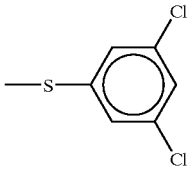 | 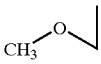 | " | " | S |
| 400 | " | " | 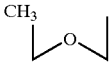 | " | " | " |
| 401 | " | 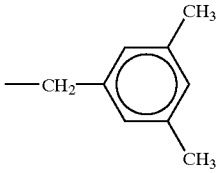 | 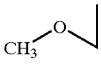 | " | " | O |
| 402 | " | " | " | " | " | S |
| 403 | " | " | 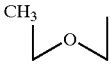 | " | " | O |
| 404 | —$CH_3$ | 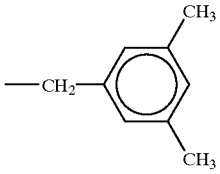 | 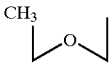 | —H | O | S |
| 405 | " | 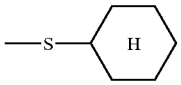 | 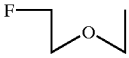 | " | " | " |
| 406 | " | 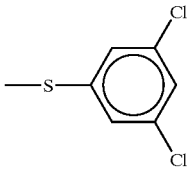 | " | " | " | " |
| 407 | " | 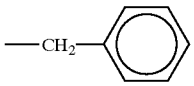 | " | " | " | " |
| 408 | " | 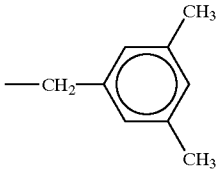 | " | " | " | O |
| 409 | " | " | " | " | " | S |

TABLE 1-continued
| | | | | | | |
|---|---|---|---|---|---|---|
| 410 | " | 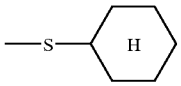 | 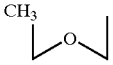 | " | " | O |
| 411 | " | 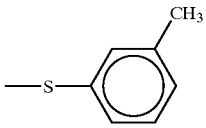 | " | " | " | S |
| 412 | " | 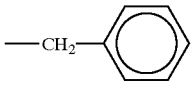 | " | " | " | " |
| 413 | " | 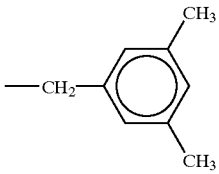 | " | " | " | O |
| 414 | " | " | " | " | " | S |
| 415 | —$CH_3$ | 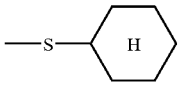 | 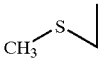 | —H | O | S |
| 416 | " | 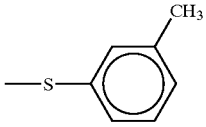 | " | " | " | " |
| 417 | " | 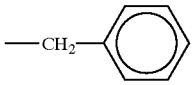 | " | " | " | " |
| 418 | " | 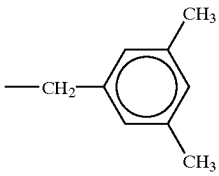 | " | " | " | O |
| 419 | " | " | " | " | " | S |
| 420 | " | 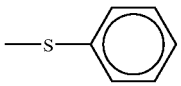 | 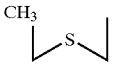 | " | " | O |
| 421 | " | " | " | " | " | S |
| 422 | —$C_2H_5$ | " | " | " | " | O |
| 423 | " | " | " | " | " | S |
| 424 | —$CH_3$ | 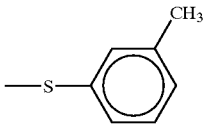 | " | " | " | O |
| 425 | " | " | " | " | " | S |

TABLE 1-continued
| | | | | | | |
|---|---|---|---|---|---|---|
| 426 | —$C_2H_5$ | 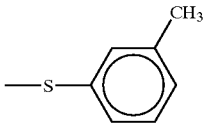 | 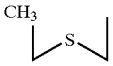 | —H | O | O |
| 427 | " | " | " | " | " | S |
| 428 | —$CH_3$ | 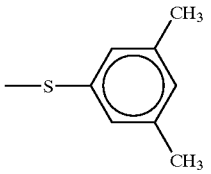 | " | " | " | O |
| 429 | " | " | " | " | " | S |
| 430 | —$C_2H_5$ | " | " | " | " | O |
| 431 | " | 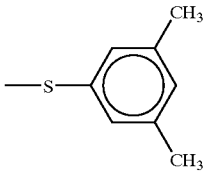 | " | " | " | S |
| 432 | —$CH_3$ | 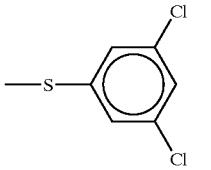 | " | " | " | O |
| 433 | " | " | " | " | " | S |
| 434 | —$C_2H_5$ | " | " | " | " | O |
| 435 | " | " | " | " | " | S |
| 436 | —$CH_3$ | 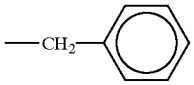 | " | " | " | O |
| 437 | —$CH_3$ | 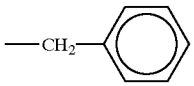 | 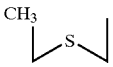 | —H | O | S |
| 438 | —$C_2H_5$ | " | " | " | " | O |
| 439 | " | " | " | " | " | S |
| 440 | —$CH_3$ | 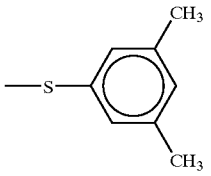 | " | " | " | O |
| 441 | " | " | " | " | " | S |

TABLE 1-continued
| | | | | | | |
|---|---|---|---|---|---|---|
| 442 | —$C_2H_5$ | 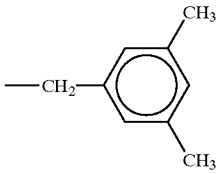 | " | " | " | O |
| 443 | " | " | " | " | " | S |
| 444 | —CH3 | 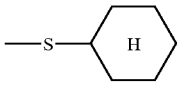 | " | " | " | O |
| 445 | " | " | " | " | " | S |
| 445 | —$C_2H_5$ | " | " | " | " | O |
| 447 | " | " | " | " | " | S |
| 448 | —$C_2H_5$ | 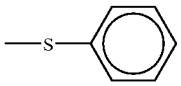 | 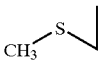 | —H | O | S |
| 449 | " | 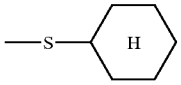 | " | " | " | O |
| 450 | " | " | " | " | " | S |
| 451 | " | 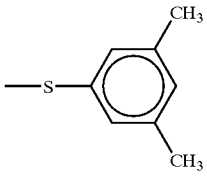 | " | " | " | O |
| 452 | " | " | " | " | " | S |
| 453 | " | 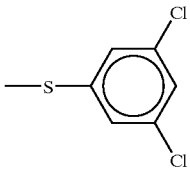 | " | " | " | O |
| 454 | " | " | " | " | " | S |
| 455 | " | 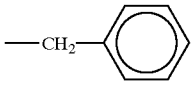 | " | " | " | O |
| 456 | " | " | " | " | " | S |
| 457 | " | 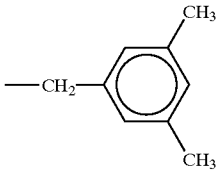 | " | " | " | O |
| 458 | " | " | " | " | " | S |
| 459 | —$C_2H_5$ | 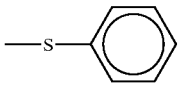 | 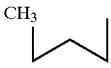 | —H | " | S |

TABLE 1-continued
| | | | | | | | |
|---|---|---|---|---|---|---|---|
| 460 | " | 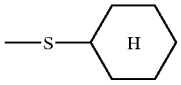 | " | " | " | O | |
| 461 | " | " | " | " | " | S | |
| 462 | " | 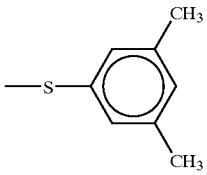 | " | " | " | O | |
| 463 | " | " | " | " | " | S | |
| 464 | " | 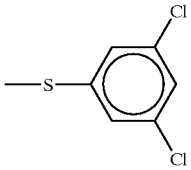 | " | " | " | O | |
| 465 | " | " | " | " | " | S | |
| 466 | " | 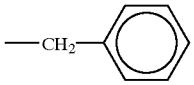 | " | " | " | O | |
| 467 | " | " | " | " | " | S | |
| 468 | " | 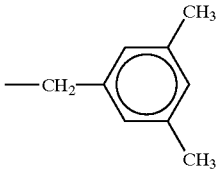 | " | " | " | O | |
| 469 | " | " | " | " | " | S | |
| 470 | $-C_2H_5$ | 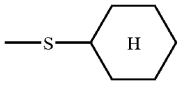 | 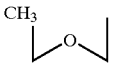 | —H | O | O | |
| 471 | " | " | " | " | " | S | |
| 472 | " | 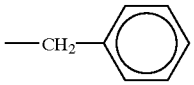 | " | " | " | O | 92.5~95 |
| 473 | " | " | " | " | " | S | |
| 474 | " | 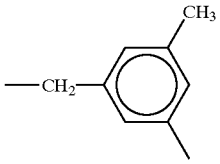 | " | " | " | O | 160~160.7 |
| 475 | " | " | " | " | " | S | |

TABLE 1-continued
| | | | | | | | |
|---|---|---|---|---|---|---|---|
| 476 | " | 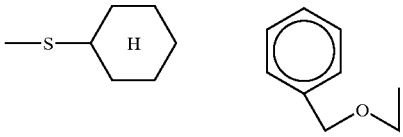 | | " | " | O | |
| 477 | " | " | " | " | " | S | |
| 478 | " | 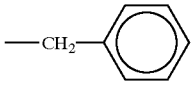 | " | " | " | O | |
| 479 | " | " | " | " | " | S | |
| 480 | " | 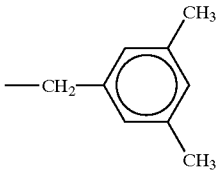 | " | " | " | O | |
| 481 | $—C_2H_5$ | 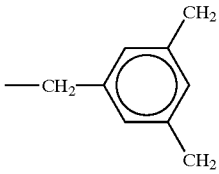 | 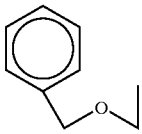 | —H | O | S | |
| 482 | " | 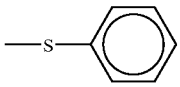 | 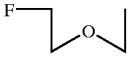 | " | " | " | |
| 483 | " | 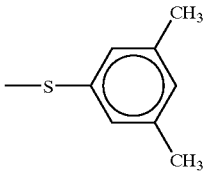 | " | " | " | O | |
| 484 | " | " | " | " | " | S | |
| 485 | $—CH_3$ | 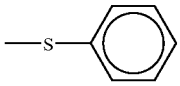 | 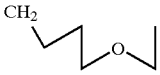 | " | " | O | 118~120 |
| 486 | " | 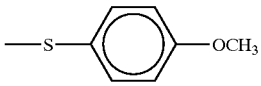 | 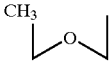 | " | " | O | |
| 487 | " | " | " | " | " | S | |
| 488 | $—C_2H_5$ | " | " | " | " | O | |
| 489 | " | " | " | " | " | S | |
| 490 | $—CH_3$ | 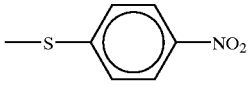 | " | " | " | O | |
| 491 | " | " | " | " | " | S | |
| 492 | $—C_2H_5$ | 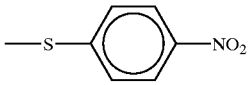 | 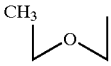 | —H | O | O | |

TABLE 1-continued
| | | | | | | | |
|---|---|---|---|---|---|---|---|
| 493 | " | " | " | " | " | S | |
| 494 | 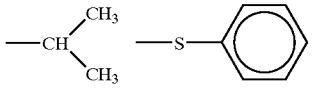 | | 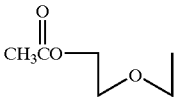 | " | " | O | |
| 495 | " | " | 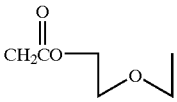 | " | " | " | |
| 496 | " | " | 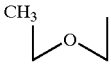 | " | " | " | 112~114 |
| 497 | " | " | " | " | " | S | 138~140 |
| 498 | " | 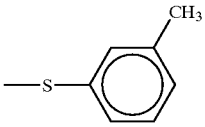 | " | " | " | O | |
| 499 | " | " | " | " | " | S | |
| 500 | " | 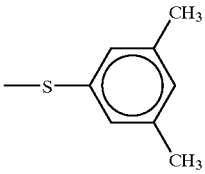 | " | " | " | O | |
| 501 | 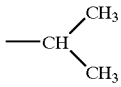 | " | 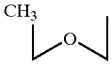 | " | " | S | |
| 502 | " | 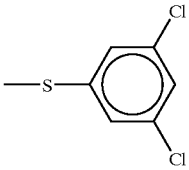 | " | " | " | O | |
| 503 | 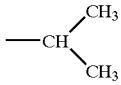 | 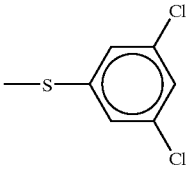 | 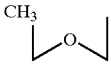 | –H | O | S | |
| 504 | " | 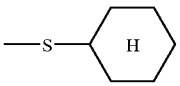 | " | " | " | O | |
| 505 | " | " | " | " | " | S | |
| 506 | " | 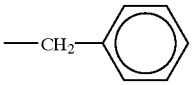 | " | " | " | O | |
| 507 | " | " | " | " | " | S | |

TABLE 1-continued
| | | | | | | | |
|---|---|---|---|---|---|---|---|
| 508 | " | 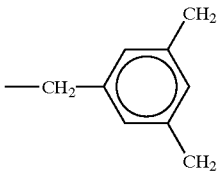 | " | " | " | O | |
| 509 | " | " | " | " | " | S | |
| 510 | " | 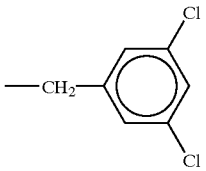 | " | " | " | O | |
| 511 | " | " | " | " | " | S | |
| 512 | " | 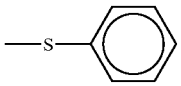 | 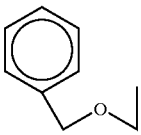 | " | " | O | 138~141 |
| 513 | " | " | " | " | " | S | 165~168 |
| 514 | 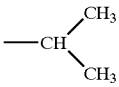 | 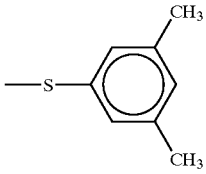 | 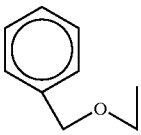 | —H | O | O | |
| 515 | " | " | " | " | " | S | |
| 516 | " | 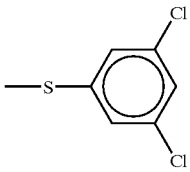 | " | " | " | O | |
| 517 | " | " | " | " | " | S | |
| 518 | " | 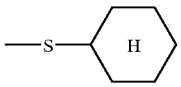 | " | " | " | O | |
| 519 | " | " | " | " | " | S | |
| 520 | " | 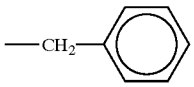 | " | " | " | O | |
| 521 | " | " | " | " | " | S | |
| 522 | " | 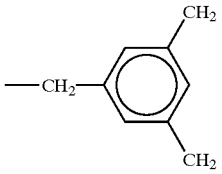 | " | " | " | O | |
| 523 | " | " | " | " | " | S | |

TABLE 1-continued
| | | | | | | |
|---|---|---|---|---|---|---|
| 524 | " | 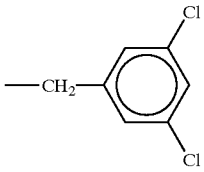 | " | " | " | O |
| 525 | 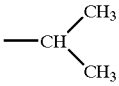 | 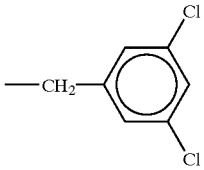 | 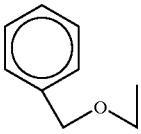 | —H | O | S |
| 526 | " | 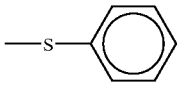 | 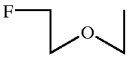 | " | " | O |
| 527 | " | " | " | " | " | S |
| 528 | " | 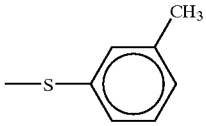 | " | " | " | O |
| 529 | " | " | " | " | " | S |
| 530 | " | 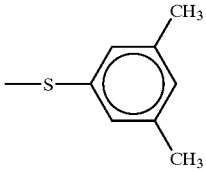 | " | " | " | O |
| 531 | " | " | " | " | " | S |
| 532 | " | 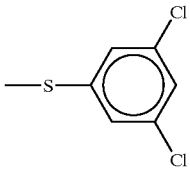 | " | " | " | O |
| 533 | " | " | " | " | " | S |
| 534 | " | 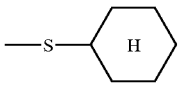 | " | " | " | O |
| 535 | " | " | " | " | " | S |
| 536 | 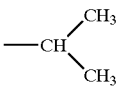 | 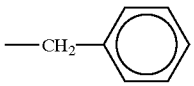 | 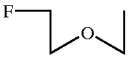 | —H | O | O |
| 537 | " | " | " | " | " | S |

TABLE 1-continued
| | | | | | | |
|---|---|---|---|---|---|---|
| 538 | " | 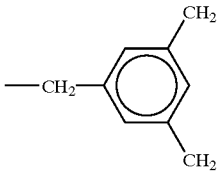 | " | " | " | O |
| 539 | " | " | " | " | " | S |
| 540 | " | 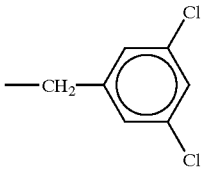 | " | " | " | O |
| 541 | " | " | " | " | " | S |
| 542 | " | 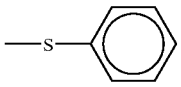 | 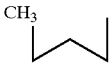 | " | " | O |
| 543 | " | " | " | " | " | S |
| 544 | " | 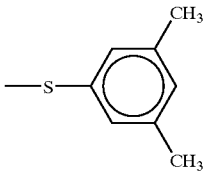 | " | " | " | O |
| 545 | " | " | " | " | " | S |
| 546 | " | 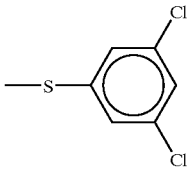 | " | " | " | O |
| 547 | 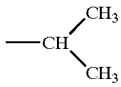 | 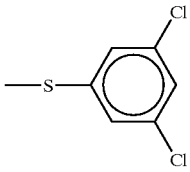 | 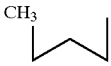 | —H | O | S |
| 548 | " | 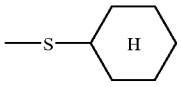 | " | " | " | O |
| 549 | " | " | " | " | " | S |
| 550 | " | 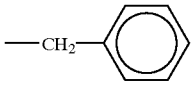 | " | " | " | O |
| 551 | " | " | " | " | " | S |

TABLE 1-continued
| | | | | | | |
|---|---|---|---|---|---|---|
| 552 | " | 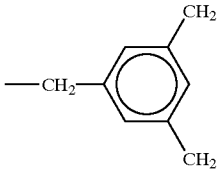 | " | " | " | O |
| 553 | " | " | " | " | " | S |
| 554 | " | 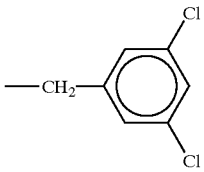 | " | " | " | O |
| 555 | " | " | " | " | " | S |
| 556 | " | 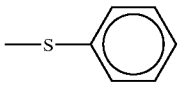 | 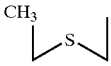 | " | " | O |
| 557 | " | " | " | " | " | S |
| 558 | 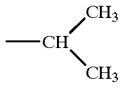 | 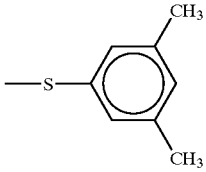 | 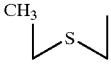 | —H | O | O |
| 559 | " | " | " | " | " | S |
| 560 | " | 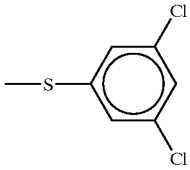 | " | " | " | O |
| 561 | " | " | " | " | " | S |
| 562 | " | 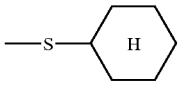 | " | " | " | O |
| 563 | " | " | " | " | " | S |
| 564 | " | 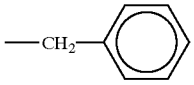 | " | " | " | O |
| 565 | " | " | " | " | " | S |
| 566 | " | 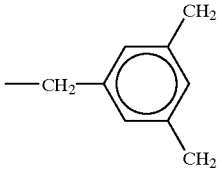 | " | " | " | O |
| 567 | " | " | " | " | " | S |

TABLE 1-continued
| | | | | | | | |
|---|---|---|---|---|---|---|---|
| 568 | " | 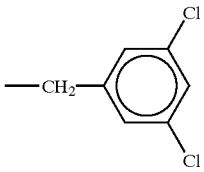 | " | " | " | O | |
| 569 | 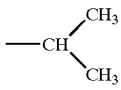 | 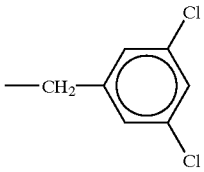 | 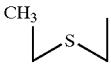 | —H | O | S | |
| 570 | | 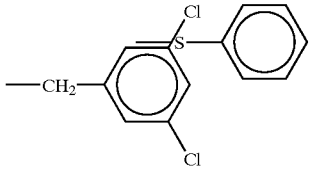 | 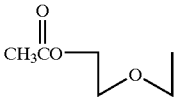 | " | " | O | |
| 571 | " | 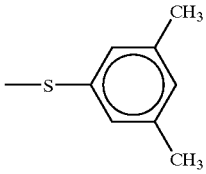 | | " | " | S | |
| 572 | " | " | 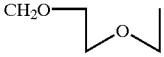 | " | " | O | |
| 573 | " | " | " | " | " | S | |
| 574 | " | 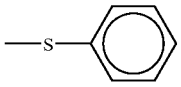 | 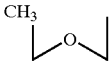 | " | " | O | 94~97 |
| 575 | " | " | " | " | " | S | 123~124 |
| 576 | " | 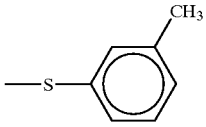 | " | " | " | O | |
| 577 | " | " | " | " | " | S | |
| 578 | " | 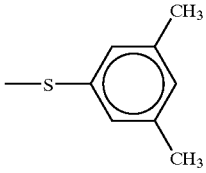 | " | " | " | O | |
| 579 | " | " | " | " | " | S | |
| 580 | 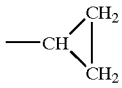 | 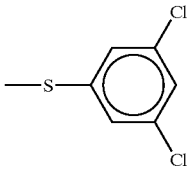 | 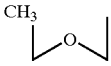 | —H | O | O | |

TABLE 1-continued
| | | | | | | |
|---|---|---|---|---|---|---|
| 581 | " | " | " | " | " | S |
| 582 | " | 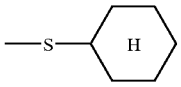 | " | " | " | O |
| 583 | " | " | " | " | " | S |
| 584 | " | 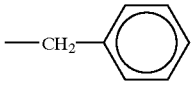 | " | " | " | O |
| 585 | " | " | " | " | " | S |
| 586 | " | 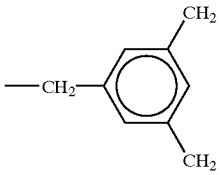 | " | " | " | O |
| 587 | " | " | " | " | " | S |
| 588 | " | 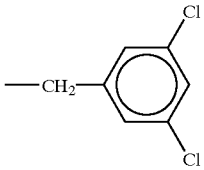 | " | " | " | O |
| 589 | " | " | " | " | " | S |
| 590 | " | 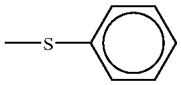 | 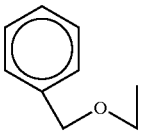 | " | " | O |
| 591 | 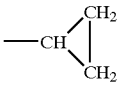 | 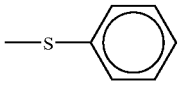 | 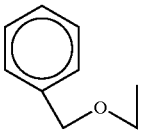 | —H | O | S |
| 592 | " | 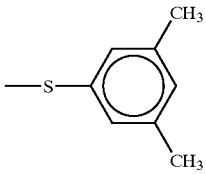 | " | " | " | O |
| 593 | " | " | " | " | " | S |
| 594 | " | 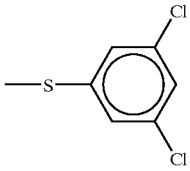 | " | " | " | O |
| 595 | " | " | " | " | " | S |

TABLE 1-continued
| | | | | | | |
|---|---|---|---|---|---|---|
| 596 | " | 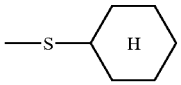 | " | " | " | O |
| 597 | " | " | " | " | " | S |
| 598 | " | 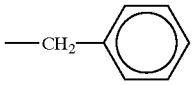 | " | " | " | O |
| 599 | " | " | " | " | " | S |
| 600 | " | 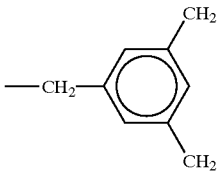 | " | " | " | O |
| 601 | " | " | " | " | " | S |
| 602 | 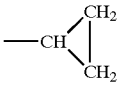 | 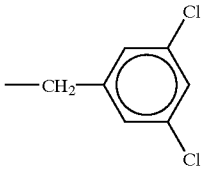 | 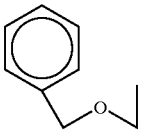 | —H | O | O |
| 603 | " | " | " | " | " | S |
| 604 | " | 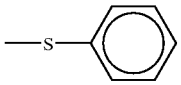 | 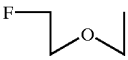 | " | " | O |
| 605 | " | " | " | " | " | S |
| 606 | " | 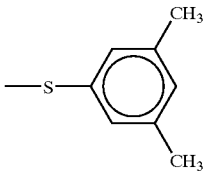 | " | " | " | O |
| 607 | " | " | " | " | " | S |
| 608 | " | 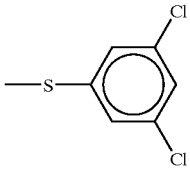 | " | " | " | O |
| 609 | " | " | " | " | " | S |
| 610 | " | 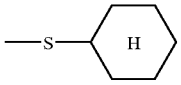 | " | " | " | O |
| 611 | " | " | " | " | " | S |
| 612 | " | 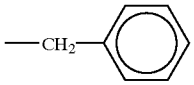 | " | " | " | O |

TABLE 1-continued
| | | | | | | |
|---|---|---|---|---|---|---|
| 613 | 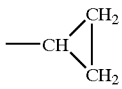 | 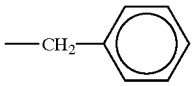 | 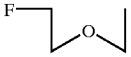 | —H | O | S |
| 614 | " | 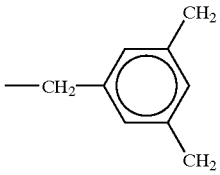 | " | " | " | O |
| 615 | " | " | " | " | " | S |
| 616 | " | 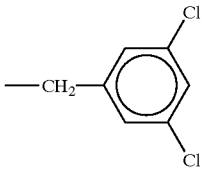 | " | " | " | O |
| 617 | " | " | " | " | " | S |
| 618 | " | 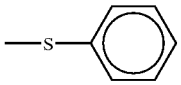 | 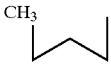 | " | " | O |
| 619 | " | " | " | " | " | S |
| 620 | " | 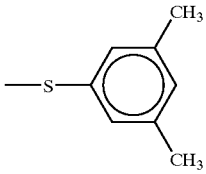 | " | " | " | O |
| 621 | " | " | " | " | " | S |
| 622 | " | 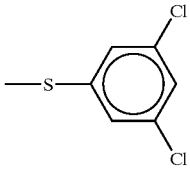 | " | " | " | O |
| 623 | " | " | " | " | " | S |
| 624 | 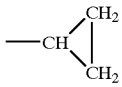 | 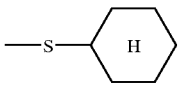 | 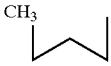 | —H | O | O |
| 625 | " | " | " | " | " | S |
| 626 | " | 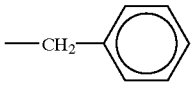 | " | " | " | O |
| 627 | " | " | " | " | " | S |
| 628 | " | 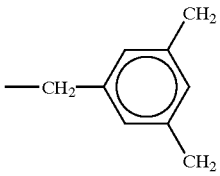 | " | " | " | O |

TABLE 1-continued
| | | | | | | |
|---|---|---|---|---|---|---|
| 629 | " | " | " | " | " | S |
| 630 | " | 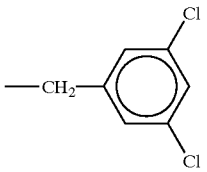 | " | " | " | O |
| 631 | " | " | " | " | " | S |
| 632 | " | 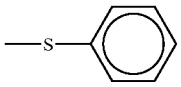 | 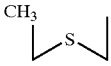 | " | " | O |
| 633 | " | " | " | " | " | S |
| 634 | " | 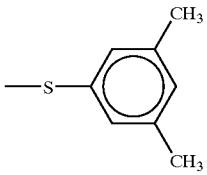 | " | " | " | O |
| 635 | 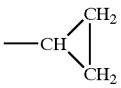 | 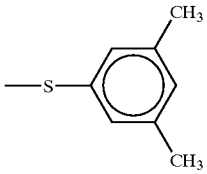 | 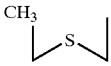 | —H | O | S |
| 636 | " | 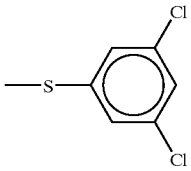 | " | " | " | O |
| 637 | " | " | " | " | " | S |
| 638 | " | 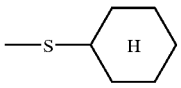 | " | " | " | O |
| 639 | " | " | " | " | " | S |
| 640 | " | 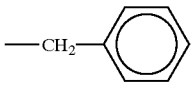 | " | " | " | O |
| 641 | " | " | " | " | " | S |
| 642 | " | 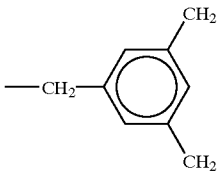 | " | " | " | O |
| 643 | " | " | " | " | " | S |

TABLE 1-continued
| | | | | | | |
|---|---|---|---|---|---|---|
| 644 | " | 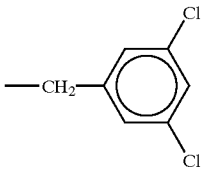 | " | " | " | O |
| 645 | " | " | " | " | " | S |
| 646 | n-$C_3H_7$ | 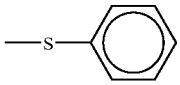 | 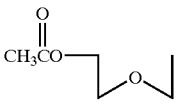 | —H | O | O |
| 647 | " | 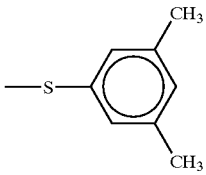 | 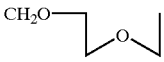 | " | " | S |
| 648 | " | 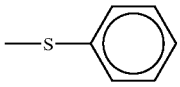 | 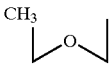 | " | " | O |
| 649 | " | " | " | " | " | S |
| 650 | " | 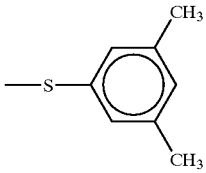 | " | " | " | O |
| 651 | " | " | " | " | " | S |
| 652 | " | 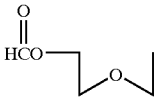 | " | " | " | O |
| 653 | " | " | " | " | " | S |
| 654 | " | 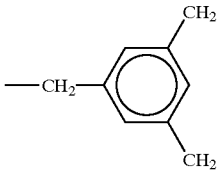 | " | " | " | O |
| 655 | " | " | " | " | " | S |
| 656 | " | 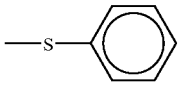 | 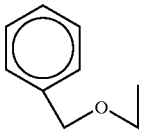 | " | " | O |
| 657 | n-$C_3H_7$ | 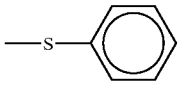 | 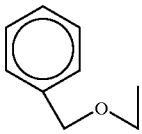 | —H | O | S |

TABLE 1-continued
| | | | | | | |
|---|---|---|---|---|---|---|
| 658 | " | 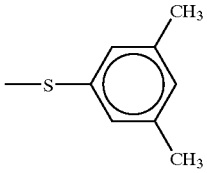 | " | " | " | O |
| 659 | " | " | " | " | " | S |
| 660 | " | 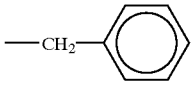 | " | " | " | O |
| 661 | " | " | " | " | " | S |
| 662 | " | 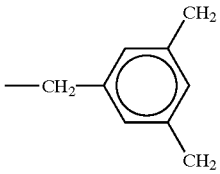 | " | " | " | O |
| 663 | " | " | " | " | " | S |
| 664 | —$CH_3$ | 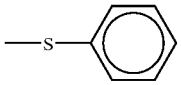 | 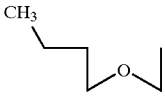 | " | " | S |
| 665 | " | 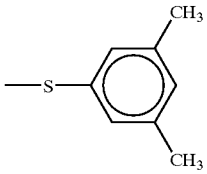 | " | " | " | O |
| 666 | " | " | " | " | " | S |
| 667 | —$CH_2CH_3$ | 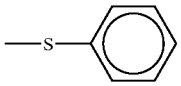 | " | " | " | O |
| 668 | —$CH_2CH_3$ | 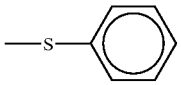 | 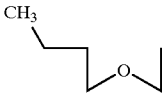 | —H | O | S |
| 669 | 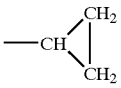 | 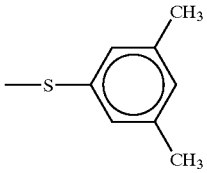 | " | " | " | O |
| 670 | " | " | " | " | " | S |
| 671 | 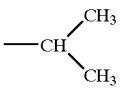 | 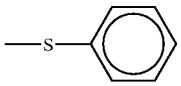 | " | " | " | O |
| 672 | " | " | " | " | " | S |

TABLE 1-continued
| | | | | | | | |
|---|---|---|---|---|---|---|---|
| 673 | " | 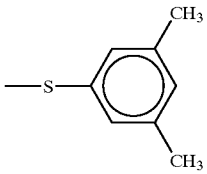 | " | " | " | O | |
| 674 | " | " | " | " | " | S | |
| 675 | $-C_2H_5$ | 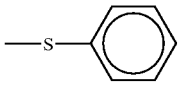 | 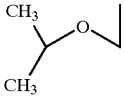 | " | " | O | 119~121 |
| 676 | " | " | " | " | " | S | 141~142 |
| 677 | " | 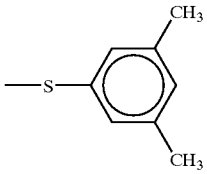 | " | " | " | O | |
| 678 | " | " | " | " | " | S | |
| 679 | $-C_2H_5$ | 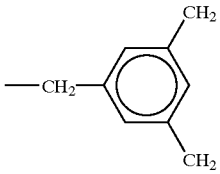 | 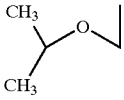 | —H | O | O | |
| 680 | " | " | " | " | " | S | |
| 681 | 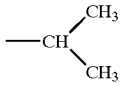 | 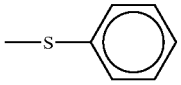 | " | " | " | O | |
| 682 | " | " | " | " | " | S | |
| 683 | " | 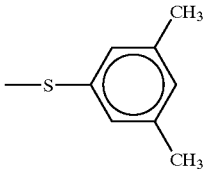 | " | " | " | O | |
| 684 | " | " | " | " | " | S | |
| 685 | $-C_2H_5$ | 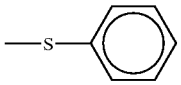 | 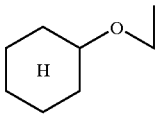 | " | " | O | 167~171 |
| 686 | " | " | " | " | " | S | 139~141 |
| 687 | 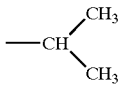 | 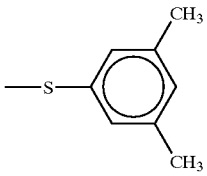 | " | " | " | O | |

TABLE 1-continued
| | | | | | | | |
|---|---|---|---|---|---|---|---|
| 688 | " | " | " | " | " | S | |
| 689 | $—C_2H_5$ | 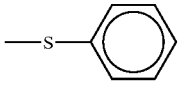 | 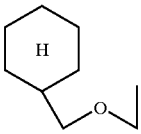 | " | " | O | 115~116 |
| 690 | $—C_2H_5$ | 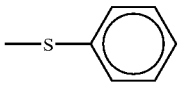 | 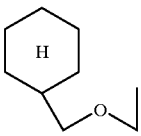 | —H | O | S | 134~135 |
| 691 | " | 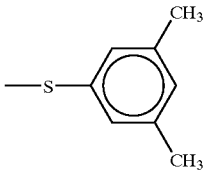 | " | " | " | O | |
| 692 | " | " | " | " | " | S | |
| 693 | " | 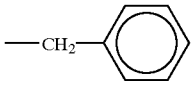 | " | " | " | O | |
| 694 | " | " | " | " | " | S | |
| 695 | " | 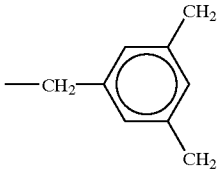 | " | " | " | O | |
| 696 | " | " | " | " | " | S | |
| 697 | 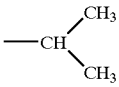 | 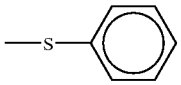 | " | " | " | O | |
| 698 | " | " | " | " | " | S | |
| 699 | $—C_2H_5$ | 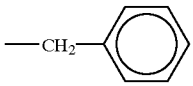 | 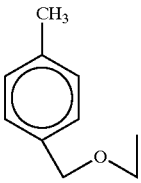 | " | " | O | |
| 700 | " | " | " | " | " | S | |
| 701 | $—C_2H_5$ | 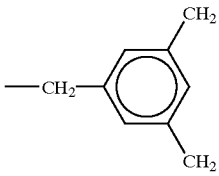 | 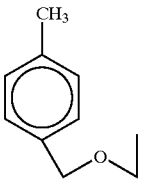 | —H | O | O | |
| 702 | " | " | " | " | " | S | |

TABLE 1-continued
| | | | | | | | |
|---|---|---|---|---|---|---|---|
| 703 | " | 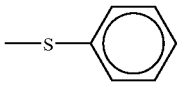 | 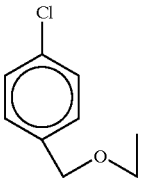 | " | " | O | |
| 704 | " | " | " | " | " | S | 132~134 |
| 705 | " | 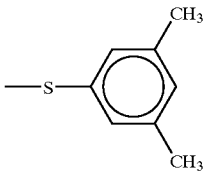 | " | " | " | O | |
| 706 | " | " | " | " | " | S | |
| 707 | " | 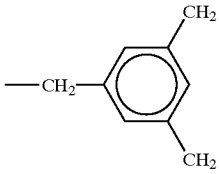 | " | " | " | O | |
| 708 | " | 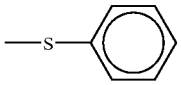 | 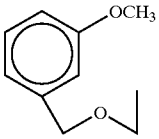 | " | " | O | |
| 709 | " | " | " | " | " | S | |
| 710 | " | 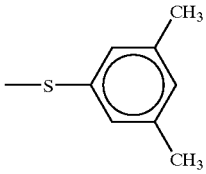 | " | " | " | O | |
| 711 | " | " | " | " | " | S | |
| 712 | $-C_2H_5$ | 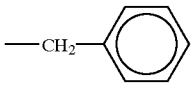 | 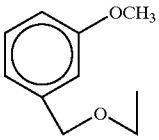 | —H | O | O | |
| 713 | " | " | " | " | " | S | |
| 714 | " | 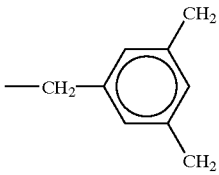 | " | " | " | O | |
| 715 | " | " | " | " | " | S | |

TABLE 1-continued
| | | | | | | |
|---|---|---|---|---|---|---|
| 716 | " | 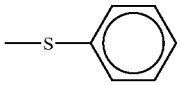 | 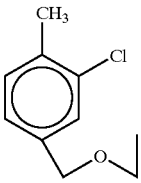 | " | " | O |
| 717 | " | " | " | " | " | S |
| 718 | " | 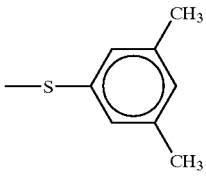 | " | " | " | O |
| 719 | " | " | " | " | " | S |
| 720 | " | 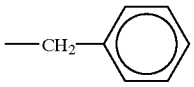 | " | " | " | O |
| 721 | " | " | " | " | " | S |
| 722 | " | 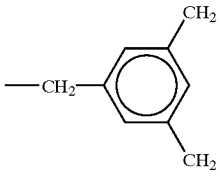 | " | " | " | O |
| 723 | $-C_2H_5$ | 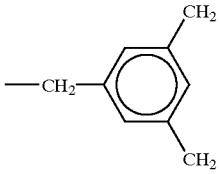 | 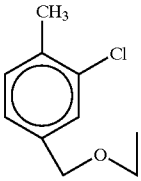 | —H | O | S |
| 724 | 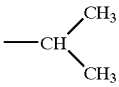 | 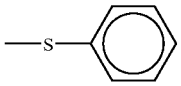 | 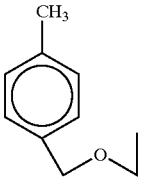 | " | " | O |
| 725 | " | " | " | " | " | S |
| 726 | " | 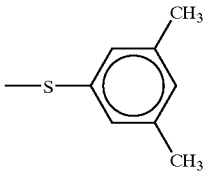 | " | " | " | O |
| 727 | " | " | " | " | " | S |
| 728 | " | 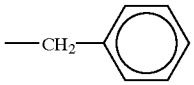 | " | " | " | O |
| 729 | " | " | " | " | " | S |

TABLE 1-continued
| | | | | | | |
|---|---|---|---|---|---|---|
| 730 | 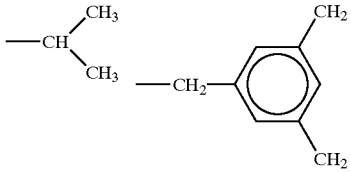 | | " | " | " | O |
| 731 | " | " | " | " | " | S |
| 732 | " | 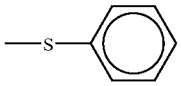 | 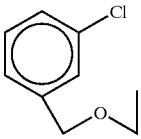 | " | " | O |
| 733 | " | " | " | " | " | S |
| 734 | 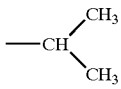 | 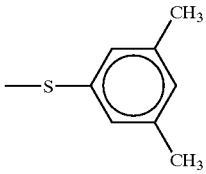 | 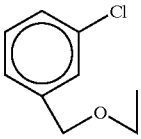 | —H | O | O |
| 735 | " | " | " | " | " | S |
| 736 | " | 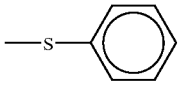 | " | " | " | O |
| 737 | " | " | " | " | " | S |
| 738 | " | 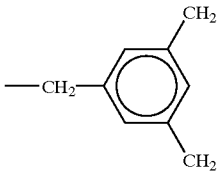 | " | " | " | O |
| 739 | " | " | " | " | " | S |
| 740 | " | 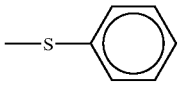 | 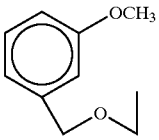 | " | " | O |
| 741 | " | " | " | " | " | S |
| 742 | " | 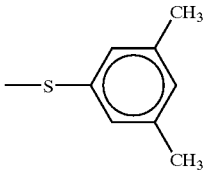 | " | " | " | O |
| 743 | " | " | " | " | " | S |
| 744 | " | 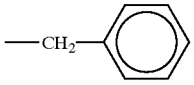 | " | " | " | O |

TABLE 1-continued
| | | | | | | | |
|---|---|---|---|---|---|---|---|
| 745 | 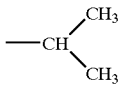 | 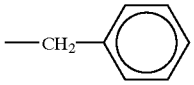 | 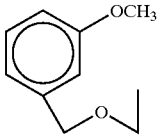 | —H | O | S | |
| 746 | " | 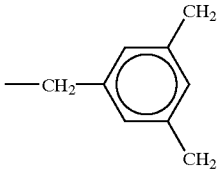 | " | " | " | O | |
| 747 | " | " | " | " | " | S | |
| 748 | $—C_2H_5$ | 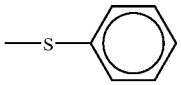 | 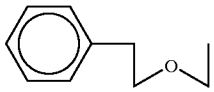 | " | " | O | 108~110 |
| 749 | " | " | " | " | " | S | 136~138 |
| 750 | " | " | 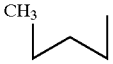 | " | " | S | |
| 751 | " | 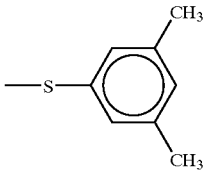 | " | " | " | O | |
| 752 | " | 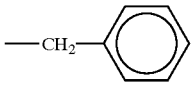 | " | " | " | O | |
| 753 | " | 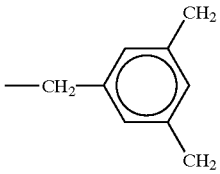 | " | " | " | S | |
| 754 | 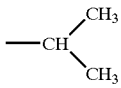 | 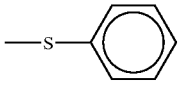 | " | " | " | O | |
| 755 | " | 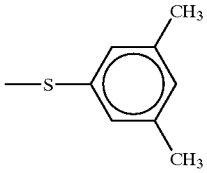 | " | " | " | S | |
| 756 | 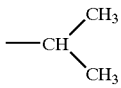 | 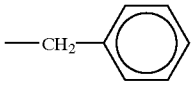 | 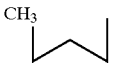 | —H | O | O | |

TABLE 1-continued
| | | | | | | |
|---|---|---|---|---|---|---|
| 757 | " | 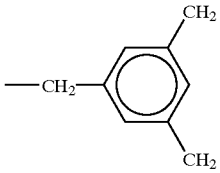 | " | " | " | S |
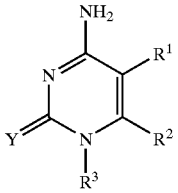
| Compound No. | $R^1$ | $R^2$ | $R^3$ | Y | Melting point (° C.) |
|---|---|---|---|---|---|
| 758 | —$CH_3$ | 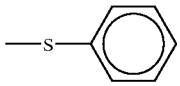 | 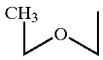 | O | |
| 759 | — | — | — | S | |
| 760 | —$C_2H_5$ | — | — | O | |
| 761 | — | — | — | S | |
| 762 | —$CH_3$ | 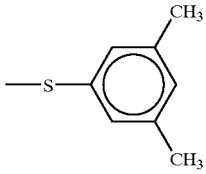 | — | O | |
| 763 | — | — | — | S | |
| 764 | —$C_2H_5$ | — | — | O | |
| 764 | — | — | — | S | |
| 766 | —$CH_3$ | 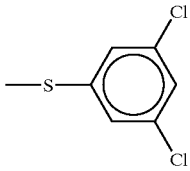 | — | O | |
| 767 | —$CH_3$ | 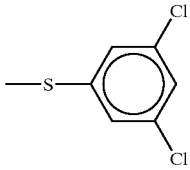 | 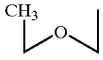 | S | |
| 768 | —$C_2H_5$ | — | — | O | |
| 769 | — | — | — | S | |
| 770 | 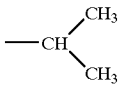 | 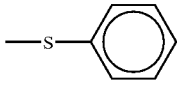 | — | O | |
| 771 | — | — | — | S | |

TABLE 1-continued
| | | | | |
|---|---|---|---|---|
| 772 | — | 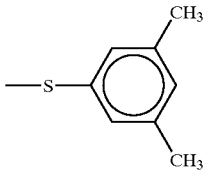 | — | O |
| 773 | — | — | — | S |
| 774 | — | 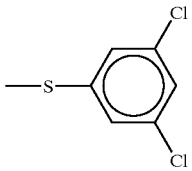 | — | O |
| 775 | — | — | — | S |
| 776 | — | 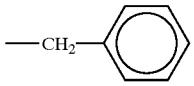 | — | O |
| 777 | — | — | — | S |
| 778 | 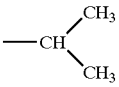 | 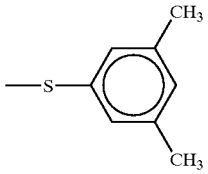 | 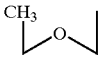 | O |
| 779 | — | — | — | S |
| 780 | $—C_2H_5$ | 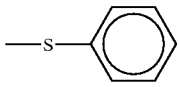 | 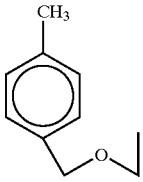 | O |
| 781 | — | — | — | S |
| 782 | — | 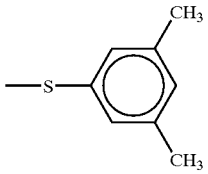 | — | O |
| 783 | — | — | — | S |
| 784 | — | 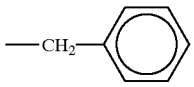 | — | O |
| 785 | — | — | — | S |
| 786 | — | 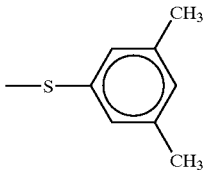 | — | O |

TABLE 1-continued
| | | | | |
|---|---|---|---|---|
| 787 | — | — | — | S |
| 788 | 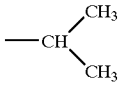 | 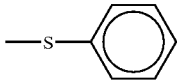 | — | O |
| 789 | 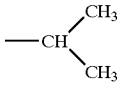 | 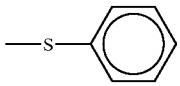 | 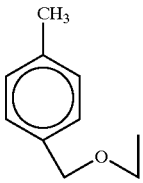 | S |
| 790 | — | | — | O |
| | | 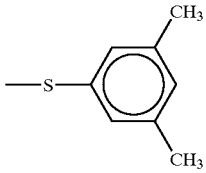 | | |
| 791 | — | — | — | S |
| 792 | — | | — | O |
| | | 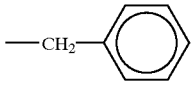 | | |
| 793 | — | — | — | S |
| 794 | — | | — | O |
| | | 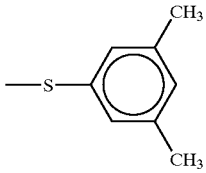 | | |
| 795 | — | — | — | S |
| 796 | 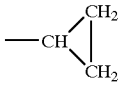 | 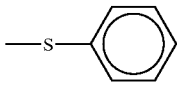 | — | O |
| 797 | — | — | — | S |

The compounds according to the invention of the formula I wherein $R^3$ represents methyl or branched alkyl or —CH2—$Z(CH_2)_n$—$R^5$ group where $R^5$ represents a hydrogen, halogen atom, azido, alkoxy, aralkyloxy, optionally substituted aryl group or the like may be prepared in accordance with the following reaction formula (1), (2) or (3):

(1)

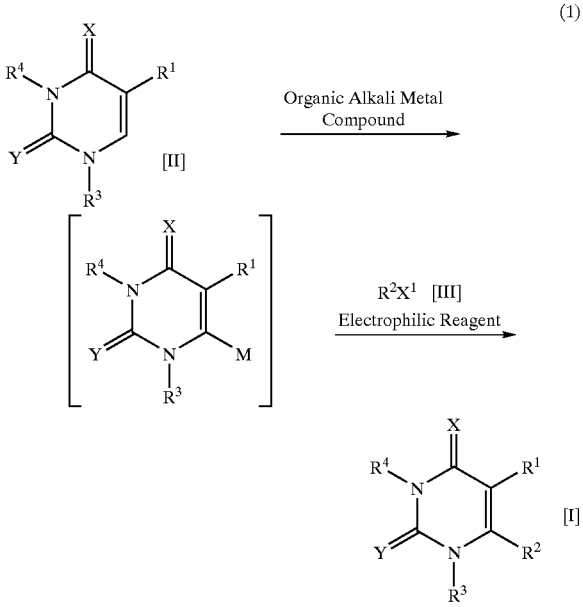

(2)

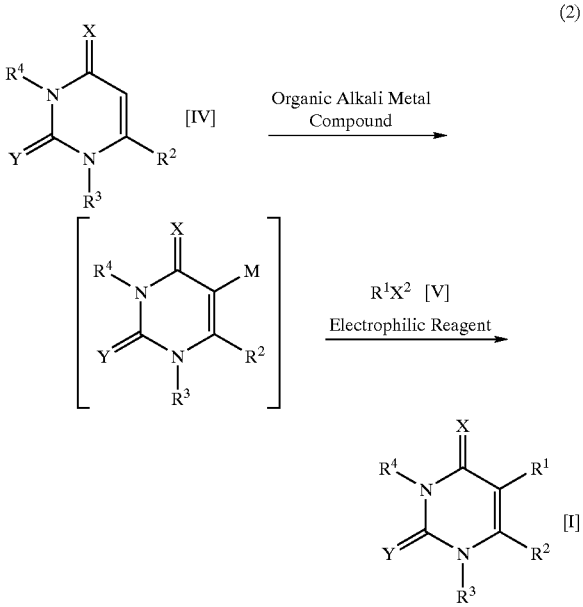

wherein $R^1$, $R^2$, $R^3$, $R^4$, X and Y have the same meanings defined hereinbefore, $X^1$ and $X^2$ represent a halogen atom, arylthio, alkoxy group or the like, and M represents an alkaline metal.

Firstly, the compound of the formula II or IV is treated with an organic alkali metal compound in an ether solvent such as diethyl ether and tetrahydrofuran at a temperature of −80° to −10° C. for 0.2 to 10 hours.

Examples of the organic alkali metal compound include potassium bistrimethylsilylamide, sodium bistrimethylsilylamide and lithium alkylamide, and particularly preferred compounds among those are lithium diisopropylamide (LDA) and lithium 2,2,6,6-tetramethylpiperidide (LTMP). Such lithium alkylamides are preferably prepared immediately before the reaction. For example, lithium dialkylamide may be prepared by reacting a secondary amine such as diisopropylamine with an alkyl lithium such as n-butyl lithium in a solvent such as diethyl ether, dioxane, tetrahydrofuran and dimethoxyethane with stirring under the atmosphere of an inert gas such as argon at −80° C. to −10° C. for 0.2 to 5 hours.

The organic alkali metal compound is usually used in an amount of 1 to 5 moles per mole of the compound of the general formula II or IV.

Then, the electrophilic reagent of the general formula $R^2X^1$ or $R^1X^2$ is added to the reaction mixture in a ratio of about 1 to 5 moles to the compound of the general formula II or IV to allow the reaction under the same condition as in the reaction with the organic alkali metal compound.

The electrophilic reagent should have a group of $R^1$ or $R^2$ defined above, and examples of this reagent includes various diaryl disulfides, arylsulfenyl chlorides, dialkyl disulfides, dicycloalkyl disulfides, alkyl halides, aralkyl halides such as benzyl bromide, acid halides such as benzoyl halide and isobutyric halide, acid anhydrides and esters thereof, arylcarbonylalkyl halides such as phenacyl chloride and the like.

The compounds of the general formula II can be prepared by a conventional method.

The compounds of the general formula IV can be prepared in accordance with the reaction formula (I) above ($R^1$=H).

(3)

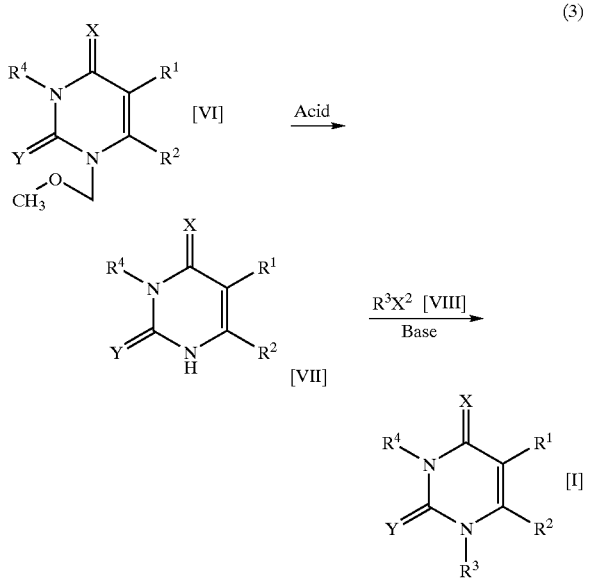

wherein $R^1$, $R^2$, $R^3$, $R^4$, X and Y have the same meanings defined hereinbefore and $X^3$ represents a halogen atom such as chlorine, bromine and iodine or sulfonyloxy group such as toluenesulfonyloxy and mesyloxy groups.

The compounds of the general formula VI are treated with an acid such as hydrochloric acid and bromic acid in a suitable solvent, for example, an alcohol such as methanol and ethanol and water at an appropriate temperature of from room temperature to 100° C. to obtain the compounds of the general formula VII.

Then, the compounds of the general formula VII are reacted with the compounds of the general formula VIII in a suitable solvent such as dimethylformamide, dimethyl sulfoxide, acetonitrile and tetrahydrofuran in the presence of a suitable base such as sodium hydride, sodium alkoxide, potassium alkoxide, potassium carbonate and sodium carbonate at a temperature of from ambient temperature to the boiling point of the solvent to obtain the compounds of the general formula I.

The starting compounds represented by the general formula VI can be prepared in accordance with the reaction formula (1) or (2).

When the objective compound has a hydroxyl group of $R^5$ or when any intermediate compound of the reactions has a hydroxyl group, the reactions of (1) and (2) should be carried out using a starting compound or intermediate compound of which hydroxyl group is protected by an appropriate protective group instead of the unprotected compound of the formula II or IV or the like, and the protective group is then eliminated to obtain the target compound.

Any protective groups conventionally used for the protection of hydroxyl group may be used for this purpose so long as it is not eliminated under the alkaline condition.

Examples of such protective group are aralkyl groups such as benzyl, trityl, monomethoxytrityl, dimethoxytrityl and trimethoxytrityl, silyl groups such as trimethylsilyl, triethylsilyl, t-butyldimethylsilyl and t-butyldiphenylsilyl, tetrahydropyranyl group and substituted alkyl groups such as methoxymethyl group. Among those protective groups, silyl groups are particularly preferred.

The introduction of the protective group can be carried out by a conventional method.

For example, the introduction of the protective silyl group may be carried out by reacting the compound having the hydroxyl group with 1 to 10 times by mole of silylating reagent such as trimethylsilyl chloride and t-butyldimethylsilyl chloride at a temperature of from 0° to 50° C. in the presence of a base such as pyridine, picoline, diethylaniline, dimethylaniline, triethylamine and imidazole in a solvent such as dimethylformamide, acetonitrile, tetrahydrofuran and a mixture of those solvents in any combination.

The elimination of the protective group may be carried out by a conventional method corresponding to the kind of the protective group, for example, acid hydrolysis, ammonium fluoride treatment or catalytic reduction.

The compounds obtained by the reactions (1), (2) or (3) which have a nitro substituted phenylthio group at the 6-position may be converted into the compounds having an amino group by hydrogenation in accordance with the reaction formula (4) below. The hydrogenation can be carried out in an organic solvent such as alcohol and acetic acid in the presence of a catalyst such as palladium/carbon at an appropriate temperature of from room temperature to 80° C.:

(4)

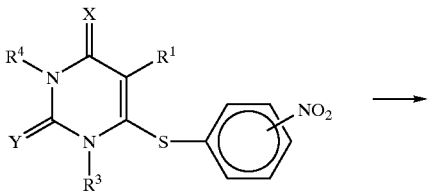

-continued

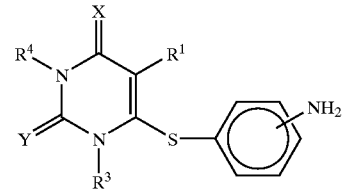

wherein the symbols have the same meanings as defined above.

The compounds having an arylthio, alkylthio or cycloalkylthio group can be converted to corresponding compounds having an arylsulfinyl, alkylsulfinyl or cycloalkylsulfinyl group by using an oxidizing agent such as hydrogen peroxide and m-chloroperbenzoic acid in accordance with the reaction formula (5) below:

(5)

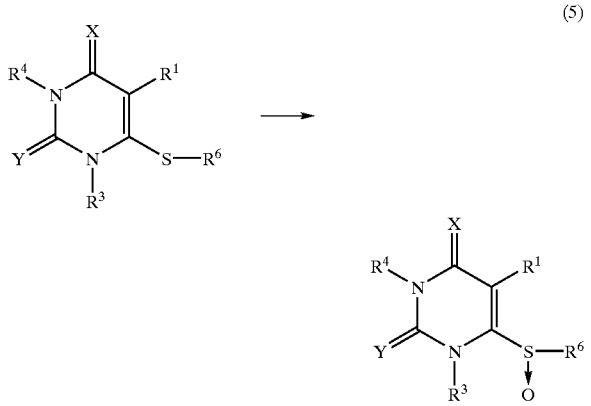

wherein $R^6$ represents an aryl, alkyl or cycloalkyl group and the other symbols have the same meanings as defined above.

The compounds having phenyl sulfoxide group can be converted into corresponding compounds having a substituted arylthio or aryloxy group by reacting with sodium arylthiolate or sodium aryloxide having various substituents on the benzene ring in an organic solvent such as tetrahydrofuran, alcohol, dimethylformamide and acetonitrile at an appropriate temperature of from room temperature to 100° C. in accordance with the reaction formula (6) below:

(6)

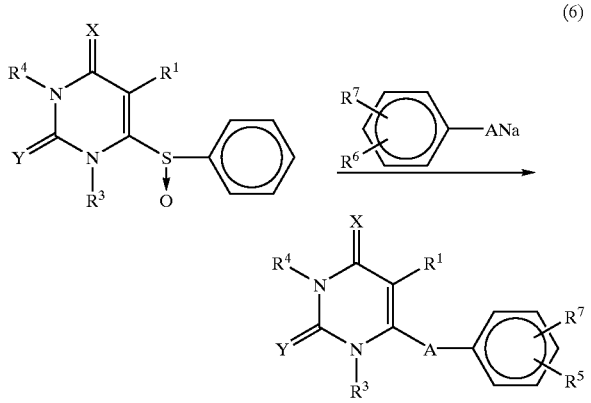

wherein A represents a sulfur or oxygen atom, $R^7$ and $R^8$ independently represent a halogen atom such as chlorine, bromine, fluorine and iodine, alkyl group such as methyl, ethyl, propyl and butyl, halogenated alkyl group such as trichloromethyl, alkoxy group such as methoxy, ethoxy, propoxy and butoxy, hydroxyl group, nitro group, amino group, cyano group and acyl group such as acetyl, and the other symbols have the same meanings as defined above.

The present compounds may be also prepared in accordance with, for example, the reaction formula (7) or (8) below:

(7)

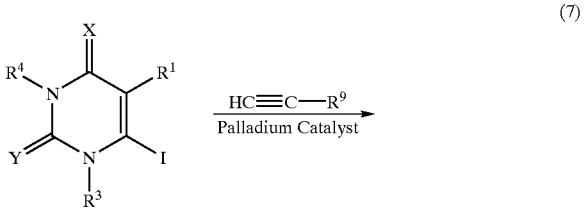

(8)

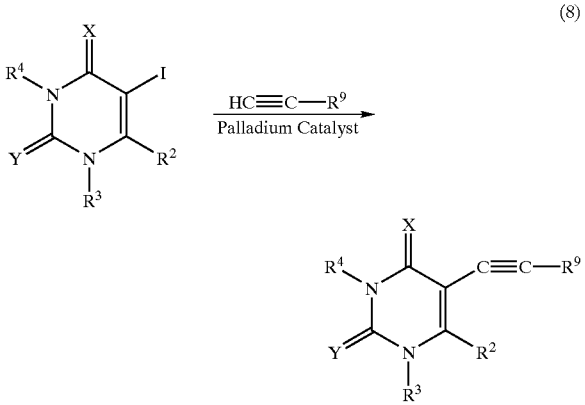

wherein $R^9$ represents an alkyl group such as methyl and ethyl, aryl group such as phenyl and toluyl, a protective group such as silyl group or the like, and the other symbols have the same meanings as defined above.

The reactions of the formulae (7) and (8) can be carried out in an amine solvent such as diethylamine and triethylamine in the presence of a palladium catalyst at an appropriate temperature of from room temperature to 70° C. The reactions may be carried but more homogeneously by adding another solvent such as acetonitrile. As the catalyst, a palladium catalyst of bis(triphenylphosphine)palladium dichloride, tetrakis(triphenylphosphine)palladium(O) and bis(diphenylphosphino)ethanepalladium dichloride can be used in combination with cuprous iodide.

The present compounds can be prepared also in accordance with the reaction formula (9) or (10) below, and the reactions may be carried out in the same manner as the reactions of the formulae (7) and (8) except that an olefin derivative of $H_2C{=}CH{-}R_{10}$ wherein $R_{10}$ represents an alkoxycarbonyl, nitrile, carbamoyl group and the like is used instead of the acetylene derivative in the reactions of the formulae (7) and (8):

(9)

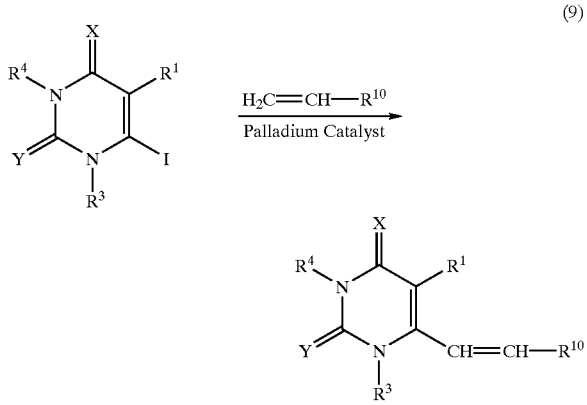

(10)

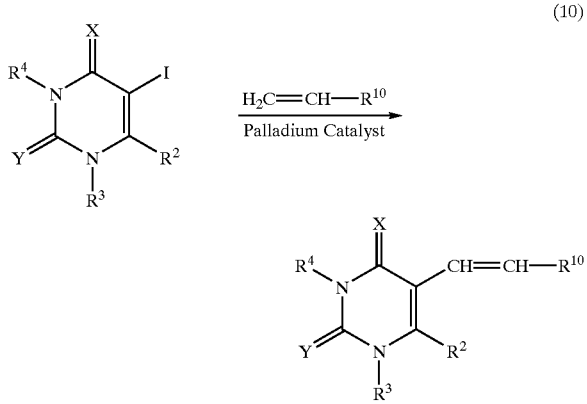

wherein the symbols have the same meanings as defined above.

The palladium catalyst may be the same as in the reaction of the formulae (7) and (8).

The compounds according to the invention can be prepared also in accordance with the reaction formula (11) below:

(11)

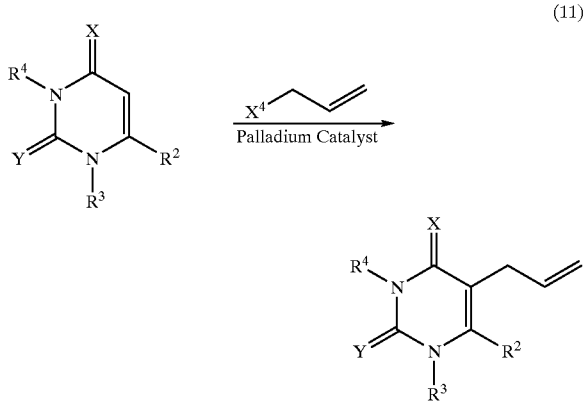

wherein $X^4$ represents a halogen atom such as chlorine, bromine and iodine, and the other symbols have the same meaning as defined above.

The compounds according to the invention can be prepared also in accordance with the reaction formula (12) or (13) below:

(12)

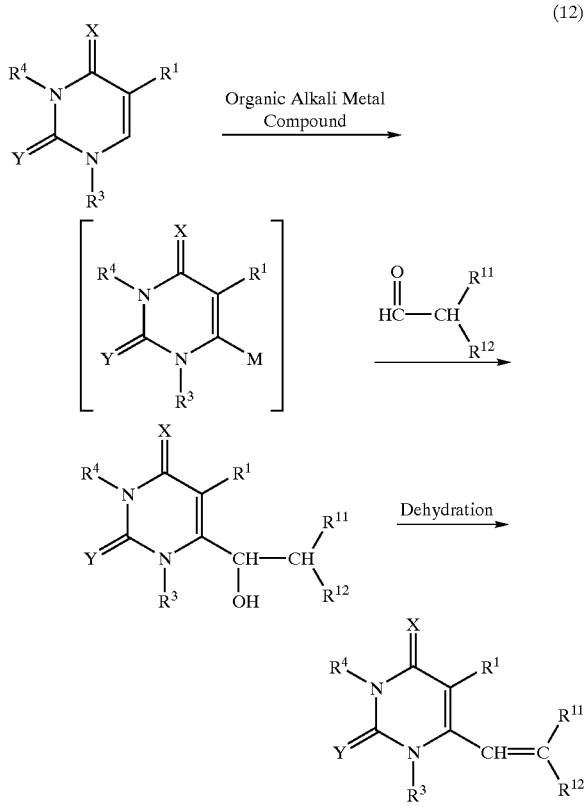

(13)

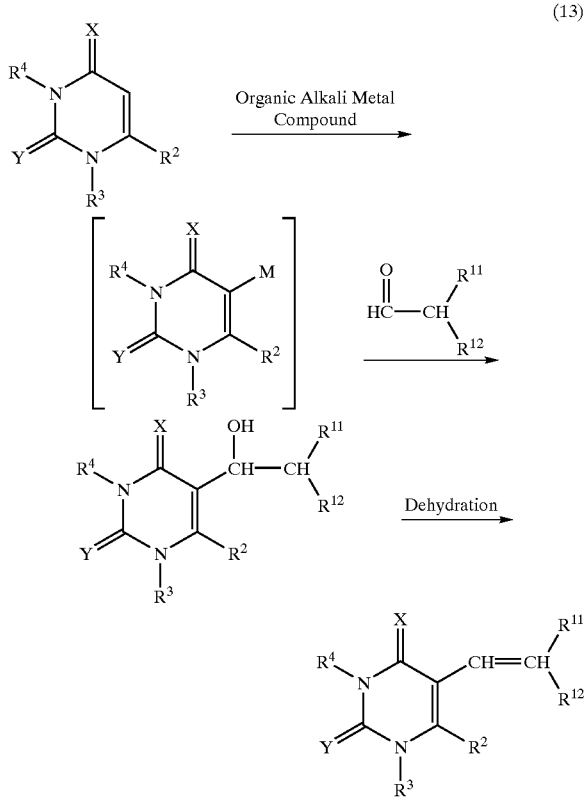

wherein the symbols have the same meanings as defined hereinbefore.

In the reactions of the formulae (12) and (13), intermediate compounds are prepared in accordance with the reaction formulae (1) and (2) as described hereinbefore except that a compound of OCH-CH($R^{11}$)($R^{12}$) wherein $R^{11}$ and $R^{12}$ independently represent a hydrogen atom, alkyl group such as methyl, ethyl and propyl or aryl group such as phenyl is used instead of the compounds $R^1X^2$ and $R^2X^1$, and then the intermediate compounds are dehydrated by a dehydrating agent such as mesyl chloride, tosyl chloride and thionyl chloride to produce the compounds according to the invention having an alkenyl group.

By hydrogenation, the alkynyl group of the compounds produced in the reactions of the formula (7) or (8) can be converted into the corresponding alkenyl or alkyl group and the alkenyl group of the compound produced in any one of the reactions formulae (9) to (13) can be converted into the corresponding alkyl group. For the reduction of alkynyl group into alkenyl group, the hydrogenation may be carried out at an appropriate temperature of from room temperature to 80° C. under hydrogen atmosphere in the presence of a catalyst such as palladium/barium sulfate, palladium/calcium carbonate, palladium/calcium carbonate/lead acetate and palladium/barium sulfate/quinoline in a solvent such as alcohol and acetic acid. For the reduction of alkenyl or alkynyl group into alkyl group, the hydrogenation may be carried out by using a catalyst such as palladium/carbon and palladium hydroxide under the same conditions as used for producing the alkenyl group.

The 6-benzyl substituted derivatives of the invention may be prepared in accordance with the reaction formula (14) below:

(14)

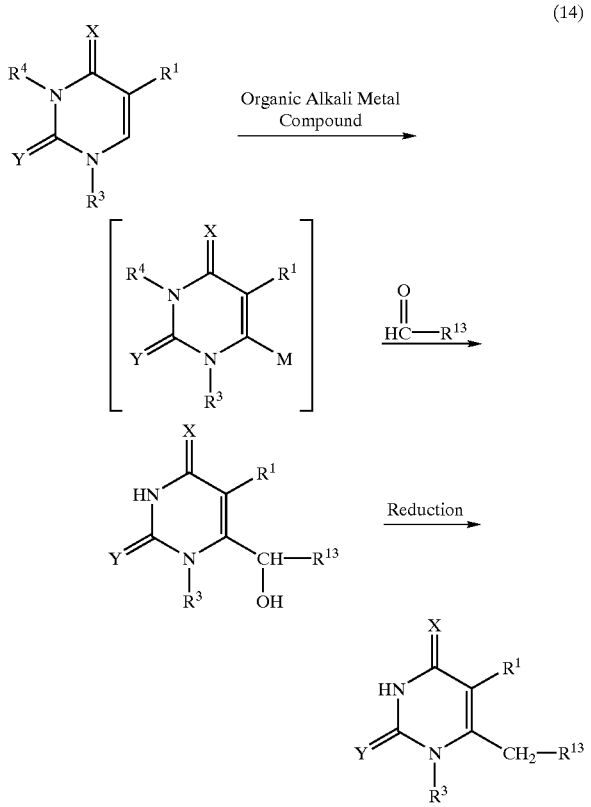

wherein the symbols have the same meanings as defined hereinbefore

In the reactions of the formula (14), intermediate compounds are prepared in the same way as the reactions of the formula (1) using OHC-$R^{13}$ where $R^{13}$ represents an optionally substituted aryl group such as phenyl instead of $R^1X^2$ and the intermediate compounds are reduced by a suitable reducing agent to convert the hydroxyl group into a hydrogen atom. The reduction can be carried out by using hydrogen gas in the presence of palladium/carbon or palladium hydroxide.

The 6-substituted acyclouridine or acyclothymidine derivatives obtained in the above-described reactions can be converted into 4-thio derivatives by heating them with 2,4-bis(4-methoxyphenyl)-1,3-dithia-2,4-diphosphetane-2,4-disulfide in a solvent such as toluene and xylene in accordance with the reaction formula (15) below:

(15)

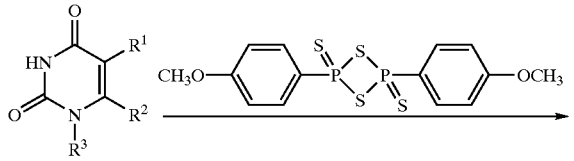

wherein the symbols have the same meanings as defined hereinbefore.

The 4-thio derivatives can be also prepared by preparing corresponding 4-chloro derivatives by chlorination of corresponding uridine or thymidine derivatives by a chlorinating agent such as phosphorous pentachloride or phosphorous oxychloride and reacting the 4-chloro derivatives with sodium bisulfide.

Further, 4-amino derivatives can be prepared by reacting the acyclouridine or thymidine derivatives with 1-(2-mesitylenesulfonyl)-3-nitro-1,2,4-triazole in the presence of diphenylphosphoric acid in a solvent such as pyridine to produce corresponding 4-(3-vitro-1,2,4-triazole) derivatives which are converted to the corresponding 4-amino derivatives by aqueous ammonia at an appropriate temperature of from room temperature to 100° C. in accordance with the reaction formula (16) below:

(16)

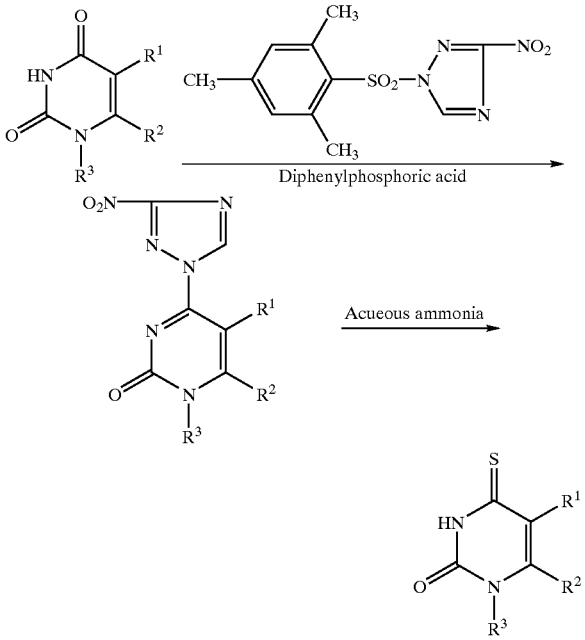

-continued

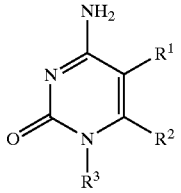

wherein the symbols have the same meanings as define hereinbefore.

Thus, the compounds of the invention represented by the formula I' are prepared as described above.

The above-obtained compounds where $R^4$ is a hydrogen atom may be converted into corresponding compounds having $R^4$ other than the hydrogen atom in accordance with the reaction formula (17) below:

(17)

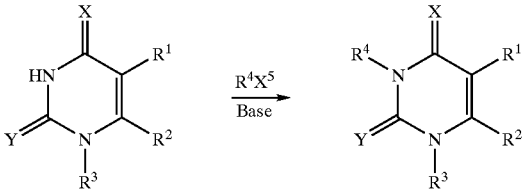

wherein X5 represents a halogen atom such as chlorine, bromine and iodine or sulfonyloxy group such as toluenesulfonyloxy and mesyloxy, and the other symbols have the same meanings as defined hereinbefore.

The reaction of the formula (17) may be carried out in a suitable solvent such as tetrahydrofuran, acetonitrile, dimethylformamide, pyridine and alcohol in the presence of a base in an amount of 1 to 2 times of the starting compound at a suitable temperature from room temperature to the boiling point of the solvent. Examples of the base include sodium alkoxide, potassium alkoxide, potassium carbonate, sodium carbonate, sodium hydride and the like.

The compounds of the invention where $R^5$ is a hydroxy group, which are obtained in any of the reactions of formula (1) to (17), may be converted into corresponding compounds having a substituted hydroxyl group in accordance with any of the reaction formulae (18) to (21) below:

(18)

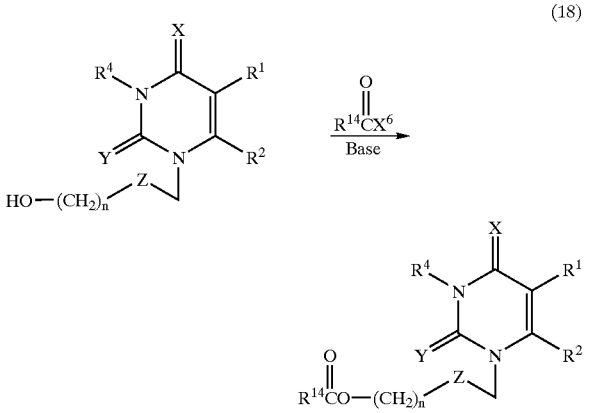

wherein R14 represents an optionally branched alkyl group, optionally substituted aryl grow or heterocyclic group, $X^6$ represents a halogen atom such as chlorine, bromine and iodine or —$OCOR^{14}$, and the other symbols have the same meanings as defined hereinbefore.

The reaction of the formula (18) may be carried out in a suitable solvent such as tetrahydrofuran, acetonitrile, dimethylformamide, pyridine, dichloromethane and chloroform in the presence of a base in an amount of 1 to 2 times of the starting compound at a suitable temperature from room temperature to the boiling point of the solvent. Examples of the base include triethylamine, pyridine, imidazole, sodium carbonate, potassium carbonate, sodium hydroxide and the like.

(19)

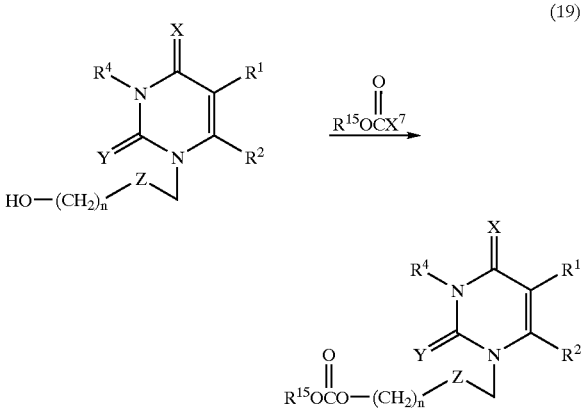

wherein $R^{15}$ represents an optionally branched alkyl group or aralkyl group, $X^7$ represents a halogen atom such as chlorine, bromine and iodine or —$OCOOR^{15}$, and the other symbols have the same meanings as defined hereinbefore.

The reaction of the formula (19) may be carried out in a suitable solvent such as tetrahydrofuran, acetonitrile, dimethylformamide, pyridine, dichloromethane and chloroform in the presence of a base in as amount of 1 to 2 times of the starting compound at a suitable temperature from room temperature to the boiling paint of the solvent. Examples of the base include triethylamine, pyridine, imidazole, sodium carbonate, potassium carbonate, sodium hydroxide and the (20)

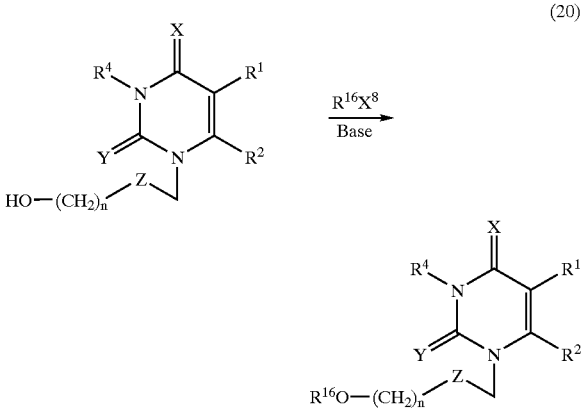

wherein $R^{16}$ represents an optionally branched alkyl group or aralkyl group, $X^8$ represents a halogen atom such as chlorine, bromine and iodine or sulfonyloxy group such as toluenesulfonyloxy and mesyloxy, and the other symbols have the same meanings as defined hereinbefore.

The reaction of the formula (20) may be carried out in a suitable solvent such as tetrahydrofuran, acetonitrile, dimethylformamide, pyridine, dichloromethane and chloroform in the presence of a base in an amount of 1 to 2 times of the starting compound at a suitable temperature from room temperature to the boiling point of the solvent. Examples of the base include triethylamine, pyridine, imidazole, sodium carbonate, potassium carbonate, sodium hydroxide and the like.

(21)

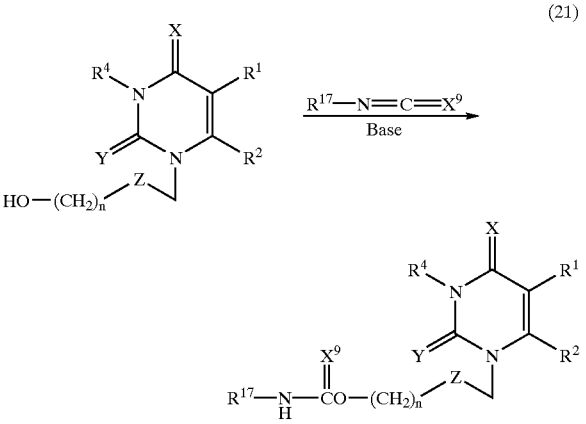

wherein $R^{17}$ represents an optionally branched alkyl group or aryl group, $X^9$ represents an oxygen or sulfur atom, and the other symbols have the same meanings as defined hereinbefore.

The reaction of formula (21) may be carried out in an appropriate solvent such as tetrahydrofuran, acetonitrile, dimethylformamide, pyridine, dichloromethane and chloroform at an appropriate temperature of from room temperature to the boiling point of the solvent.

The compounds of the present invention obtained as described hereinbefore and represented by the formula I or I' may be separated and purified by any of the conventional methods for the separation and purification of nucleosides, for example, recrystallization, adsorption chromatography, ion exchange chromatography and the like.

The compound of the invention represented by the formula I or I' may be converted into a pharmaceutically acceptable salt thereof by a conventional method. Such salt may be, for example, an alkali metal salt such as sodium or potassium salt, alkaline earth salt such as magnesium salt, ammonium salt or alkylammonium salt such as methylammonium, dimethylammonium, trimethylammonium, tetramethylammonium salt or the like.

The compounds according to invention can be administered to human beings via any route, oral, rectal, parenteral or local for the prevention or treatment of the infection of viruses such as retrovirus. The administration dose of the compounds according to the invention may be determined according to age, physical condition, body weight and the like of a patient to be treated; however, a suitable daily does of the compounds is 1 to 100 mg/(body weight)kg, preferably 5 to 50 mg/(body weight)kg and it is administered in one to several times.

The compound of the invents is generally prepared in a pharmaceutical composition with a suitable carrier, excipient and other additives. Either a liquid carrier or solid carrier may be suitably used for the present antiviral agent.

Examples of the solid carrier are lactose, kaolin, sucrose, crystalline cellulose, corn starch, talc, agar, pectin, stearic acid, magnesium stearate, lecithin, sodium chloride and the like.

Examples of the liquid are glycerin, peanut oil, polyvinyl pyrrolidone, olive oil, ethanol, benzyl alcohol, propylene glycol, water and the like.

The present antiviral agent may be made in various forms. For example, it may be in the form of a tablet, powder, granule, capsule; suppository, troche or the like when a solid carrier is used, and it may be also in the form of syrup, emulsion, soft gelatin capsule, cream, gel, paste, spray, injection solution, or the like when a liquid carrier is used.

The novel 6-substituted ayclopyrimidine nucleoside derivatives according to the sent invention have an effective antiviral activity against viruses such as retrovirus and have a relatively low toxicity against the host cell, hence the derivatives of the invention are extremely useful as an active ingredient of antiviral agent.

EXAMPLE

The present invention will be further illustrated hereinafter by way of examples, but these examples do not limit the invention and many variations and modifications can be made without departing from the scope of the present invention.

The numbers of the compounds used in the description of the examples correspond to those used in Table 1.

The starting compounds used in the examples such as

1-[(2-hydroxyethoxy)methyl]-6-phenylthio-2-thiothymine,

1-[(2-hydroxyethoxy)methyl]-6-phenylthiothymine,

1-[(2-hydroxyethoxy)methyl]-6-(m,m'-dimethylphenylthio)-2-thymine,

1-[(2-hydroxyethoxy)methyl]-6-(m,m'-dimethylphenylthio)-2-thiothymine,

1-[(2-hydroxyethoxy)methyl]-6-(m,m'-dichlorophenylthio)-thymine,

1-[(2-hydroxyethoxy)methyl]-6-benzylthymine,

1-[(2-hydroxyethoxy)methyl]-6-cyclohexylthiothymine,

1-[(2-hydroxyethoxy)methyl]-6-m-tolylthiothymine and the like were produced according to the methods described in the examples of PCT International Application WO89/09213.

EXAMPLE 1

Preparation of 1-[(2-acetoxyethoxy)methyl]-6-phenylthio-2-thiothymine (compound No. 1)

To 2 ml of pyridine, 0.31 g (1.0 mmole) of 1-[(2-hydroxyethoxy)methyl]-6-phenylthio-2-thiothymine and 0.10 ml (1.1 mmol of acetic anhydride were added under a flow of nitrogen, allowed to react for 2 hours at room temperature, concentrated to dryness under reduced pressure and crystallized from ethanol/water to obtain 0.62 g of the target compound (Yield: 88%).

EXAMPLES 2–6

Using the following compounds in place of 1-[(2-hydroxyethoxy)methyl]-6-phenylthio-2-thiothymine in Example 1, Compounds Nos.2 to 6 in Table 1 were obtained in the same manner as Example 1:

1-[(2-hydroxyethoxy)methyl]-6-phenylthiothymine,

1-[(2-hydroxyethoxy)methyl]-6-(m,m'-dimethylphenylthio)thymine,

1-[(2-hydroxyethoxy)methyl]-6-(m,m'-dimethylphenylthio)-2-thiothymine,

1-[(2-hydroxyethoxy)methyl]-6-(m,m'-dichlorophenylthio)thymine, and

1-[(2-hydroxyethoxy)methyl]-6-benzylthymine.

EXAMPLES 7–13

Compounds Nos.7 to 13 in Table 1 were prepared in the same manner as Example 2 by using ethyl formats, i-butyryl chloride, pivaloyl chloride, decanoyl chloride, cyclohexanecarbonyl chloride, benzoyl chloride or nicotinyl chloride respectively in place of acetic anhydride in Example 2.

EXAMPLE 14

Compound No. 14 was prepared in the same manner as Example 2 by using t-butoxycarbonyl chloride in place of acetic anhydride in Example 2.

EXAMPLE 15

Compound No. 15 was obtained in the same manner as Example 2 by using 1-[(2-hydroxyethoxy) methyl]-6-cyclohexylthiothymine and benzyloxycarbonyl chloride in place of 1-[(2-hydroxyethoxy)methyl]-6-phenylthiothymine and acetic anhydride in Example 2 respectively.

EXAMPLE 16

Preparation of 1-[(2-phenylcarbamoyloxyethoxy) methyl]-6-m-tolylthiothymine (Compound No. 16)

To 2 ml of pyridine, 0.32 g (1.0 mmole) of 1-[(2-hydroxyethoxy)methyl]-6-m-tolylthiothymine and 0.12 ml (1.1 mmole) of phenyl isocyanate were added under a flow of nitrogen allowed to react for 18 hours at room temperature. The reaction mixture was concentrated to dryness under reduced pressure and crystallized from acetone/water to obtain 0.24 g of the target compound (Yield: 54%).

EXAMPLE 17 and 18

Compounds Nos.17 and 18 were prepared in the same manner as Example 16 by using ethyl isocyanate or phenyl thioisocyanate respectively in place of phenyl isocyanate.

EXAMPLE 19

Preparation of 1-[(2-benzyloxyethoxy)methyl]-6-phenylthiothymine (Compound No. 19)

To 4 ml of tetrahydrofuran, 0.17 g (4.2 mmol) of sodium hydride was added under a nitrogen flow, and stirred to form a suspension. To this suspension, a solution of 0.62 g (2.0 mmole) of 1-[(2-hydroxyethoxy)methyl]-6-phenylthiothymine in 2 ml of tetrahydrofuran was added slowly to react for 45 minutes at room temperature. The resultant was added with 0.24 ml (2.0 mmol) of benzyl bromide and 7.4 g (20 $\mu$mol) of tetrabutylammonium iodide and allowed to react for 15 hours. The reaction mixture was neutralized with acetic acid and distributed between chloroform and saturated aqueous solution of sodium by hydrogencarbonate, and the chloroform layer was concentrated to dryness under reduced pressure. The residue was dissolved in a small amount of chloroform, adsorbed on a silica gel column and eluted with 1% methanol/chloroform. The eluate was concentrated and crystallized from diethyl ether/hexane to obtain 0.64 g of the target compound (Yield: 80%).

EXAMPLES 20–21

Compounds Nos.20 and 21 were prepared in the same manner as Example 19 by using methyl bromide or bromopentane respectively in place of benzyl bromide.

EXAMPLE 22

Preparation of 1-(methoxymethyl)-6-phenylthiothymine (Compound No. 22)

To 250 ml of methylene chloride, 25 g (0.20 mol) of thymine and 109 ml (0.44 mol) of bistrimethylsilylacetamide were added under a nitrogen flow, and stirred for 2.5 hours at room temperature. To this mixture, 24 g (0.30 mole) of chloromethyl methyl ether and 0.59 g (1.6 mmol) of tetrabutylammonium iodide were added and heated under reflux for 1.5 hours. Then, the reaction mixture was added with 400 ml of methanol and 100 ml of water slowly and concentrated under reduced pressure. The residue was crystallized from ethyl acetate to obtain 1-(methoxymethyl)-thymine. Then, 119 ml of lithium diisopropylamide (0.25 mol) solution in tetrahydrofuran (2.1M) was added to 335 ml of tetrahydrofuran under a nitrogen flow at −70° C., to which a suspension of 17.0 g (0.10 mol) 1-(methoxymethyl) thymine in 107 ml of tetrahydrofuran added dropwise over 30 minutes. After stirring for 2.5 hours at −70° C., the reaction mixture was with a solution of 43.6 g of diphenyl disulfide in 49 ml of tetrahydrofuran dropwise over 20 minutes and allowed to react for 20 minutes. The reaction mixture was added with 35 ml of acetic acid, brought to room temperature and then added with 1 l of ethyl acetate. The mixture was washed with water (100 ml×5) and saturated solution of sodium hydrogencarbonate (twice), dried on magnesium sulfate and concentrated under reduced pressure. The residue was crystallized from ethanol to obtain 20 g of the target compound (Yield: 73%).

EXAMPLES 23–26

Compounds Nos.23 to 26 were prepared in the same manner as Example 22 by using 1-(ethoxymethyl)thymine, 1-[(2-azidoethoxy) methyl]thymine, 1-[(2-fluoroethoxy) methyl]thymine or 1-[(2-chloroethoxy)methyl]thymine respectively in place of 1-(methoxymethyl)thymine.

EXAMPLE 27

Preparation of 6-phenylthiothymine (Compound No. 27)

To 100 ml of concentrated hydrochloric acid, 17.2 g (62 mmole) of 1-(methoxymethyl)-6-phenylthiothymine was added and allowed to react for 2 hours at 80° C. The reaction mixture was concentrated under reduced pressure and crystallized from ethanol to obtain 3.8 g of the target compound (Yield: 26%).

EXAMPLE 28

Preparation of 1-methyl-6-phenylthiothymine (Compound No. 28)

To 1 ml of dimethyl sulfoxide, 20 mg (85 μmol) of 6-phenylthiothymine, 2.5 μl (40 μmol) of methyl iodide and 12 mg (85 μmol) of potassium carbonate were added and allowed to react for 6 hours at 80° C. The reaction mixture was concentrated under reduced pressure and adsorbed on a silica gel column and eluted with 1% methanol/chloroform. The eluate was concentrated and crystallized from diisopropyl ether to obtain 5.0 mg of the target compound (Yield: 51%).

EXAMPLES 29–30

Compounds Nos.29 and 30 were prepared in the same manner as Example 28 by using ethyl tosylate or n-butyl iodide respectively in place of methyl iodide.

EXAMPLE 31

Preparation of 1-(4-hydroxybutyl) -6-phenylthiothymine (Compound No. 31)

To 2 ml of dimethyl sulfoxide, 468 mg (2.0 mmol) of 6-phenythiothymine, 358 mg (1.0 mmol) of 4-(t-butyldimethylsiloxy)-butyl-p-toluenesulphonate and 276 mg (2.0 mmol) of potassium carbonate were added and heated to react for 4 hours at 80° C. The reaction mixture was concentrated under reduced pressure, added with methanol and filtered. The filtrate was concentrated under reduced pressure, added with 20 ml of tetrahydrofuran and 1 ml of 1N hydrochloric acid and stirred for 90 minutes. The reaction mixture was concentrated under reduced pressure and adsorbed on a silica gel column and eluted with 2% methanol/chloroform The eluate was concentrated and crystallized from acetone/hexane to obtain 12.0 mg of the target compound (Yield: 4%).

EXAMPLE 32

Preparation of 1-(methylthiomethyl)-6-phenylthiothymine (Compound No. 32)

To 4 ml of dimethylformamide, 0.17 ml (2.0 mmol) of chloromethylmethylsulfide, 0.47 g (2.0 mmol) of 6-phenylthiothymine, 0.56 ml (2.0 mmol) of triethylamine were added and allowed to react for 22 hours at room temperature. The reaction mixture was concentrated under reduced pressure and the residue was adsorbed on a silica gel column and eluted with chloroform. The eluate was concentrated and crystallized from ethyl acetate to obtain 45 mg of the target compound (Yield: 8%).

EXAMPLE 33

Preparation of 1-[(2-hydroxyethoxy)methyl]-3-benzyl-6-phenylthiothymine (Compound No. 33)

To 2 ml of dimethylformamide 0.62 g (2.0 mmol) of 1-[(2-hydroxyethoxy)methyl]-6-penylthiothymine, 0.26 ml (2.2 mmol) of benzyl bromide and 0.38 ml (2.2 mmol) of ethyldiisopropylamine were added and allowed to react for 5 days at room temperature under nitrogen atmosphere. The reaction mixture was concentrated under reduced pressure and the residue was adsorbed on a silica gel column and eluted with 1% methano/chloroform to obtain 0.24 g of the target compound (Yield: 30%).

EXAMPLE 34

Compounds No. 34 was prepared in the same manner as Example 33 by using methyl iodide in place of benzyl bromide.

EXAMPLE 35

Preparation of 1-ethoxymethyl-5-ethyl-6-phenylthiouracil (Compound No. 247)

To 100 ml of methylene chloride 5.1 g (40 mmol) of 5-ethyluracil and 22 ml (0.88 mmol) of bistrimethylsilylacetamide were added under a nitrogen atmosphere and stirred for 40 minutes at room temperature. To this mixture, 4.1 ml (88 mmole) of chloromethyl yl ether and 0.15 g (0.4 mmol) of tetrabutylammonium iodide were added and heated under reflux for 15 hours. Then, the reaction mixture was poured carefully into 50 ml of saturated aqueous solution of sodium hydrogencarbonate and filtered through Celite. The organic layer was washed with water, dried on magnesium sulfate and concentrated under reduced pressure. The residue was crystallized from ethyl acetate to obtain 6.4 g of (ethoxymethyl) 5-ethyluracil (Yield: 81%).

Then, 2.2 ml of lithium diisopropylamide (4.4 mmol) solution in tetrahydrofuran (2.1M) was added to 6 ml of tetrahydrofuran under a nitrogen atmosphere at −70° C., to which a solution of 0.40 g (2.0 mmol) of 1-ethoxymethyl-5-ethyluracil in 3 ml of tetrahydrofuran was added dropwise over 15 minute. After stirring for 1 hour at −70° C., the reaction mixture was added with a solution of 0.57 g of diphenyl disulfide in 2 ml of tetrahydrofuran dropwise over 10 minutes and allowed to react for 30 minutes. The reaction mixture was added with 1 ml of acetic acid, brought to room temperature and then added with 30 ml of ethyl acetate. The mixture was washed with water (3 mix 5) and saturated aqueous solution of sodium hydrogencarbonate (twice), dried on magnesium sulfate and' concentrated under reduced pressure. The residue was purified by silica gel chromatography (ethyl acetate/hexane=3:17) and crystallized from ethyl acetate to obtain 0.61 g of 1-ethoxymethyl-5-ethyl-6-phenylthiouracil (Yield: 32%).

EXAMPLE 36

Compound No. 357 was obtained in the same way as Example 35 by using 3,3',5,5'-tetramethylphenyl disulfide in place of diphenyl disulfide.

EXAMPLE 37

Preparation of 1-ethoxymethyl-5-ethyl-6-phenylthio-2-thiouracil (Compound No. 358)

To 100 ml of methylene chloride, 5.1 g (40 mmol) of 2-thiouracil and 22 ml (88 mmol) of bistrimethylsilylacetamide were added under a nitrogen atmosphere, and stirred for 40 minutes at room temperature. To this mixture, 8.2 ml (88 mmole) of chloromethyl ethyl ether and 0.15 g (0.4 mmol) of tetrabutylammonium iodide were added and heated under reflux for 15 hours. Then, the reaction mixture was poured carefully into 50 ml of saturated aqueous solution of sodium hydrogencarbonate and filtered through Celite. The organic layer was washed with water, dried on magnesium sulfate and concentrated under reduced pressure. The residue was crystallized from ethyl acetate to obtain 1.1 g of 1-ethoxymethyl-2-thiouracil (Yield: 15%).

Then, 3.3 ml lithium diisopropylamide solution in tetrahydrofuran (2.1M) was added to 9 ml of tetrahydrofuran under a nitrogen atmosphere at −70° C., to which a solution of 0.56 g (3.0 mmol) of 1-ethoxymethyl-2-thiouracil in 3 ml of tetrahydrofuran was added dropwise over 15 minutes. After stirring for 1 hour at −70° C., the reaction mixture was added with a solution of 0.85 g (3.9 mmol) of diphenyl disulfide in 1 ml of tetrahydrofuran dropwise over 10 minutes and allowed to react for 20 minutes. The reaction mixture was added with 1 ml of acetic acid, brought to room temperature and then added with 30 ml of ethyl acetate. The mixture was washed with water (3 ml×5) and saturated aqueous solution of sodium hydrogencarbonate (twice), dried on magnesium sulfate and concentrated under reduced pressure. The residue was purified by silica gel chromatography (ethyl acetate/hexane=3:17), crystallized from ethyl acetate to obtain 0.64 g of 1-ethoxymethyl-6-phenylthio-2-thiouracil (Yield: 73%).

Then, 2.1 ml of 1.6M butyl lithium (3.4 mmol) solution in hexane was added to a solution of 0.57 ml (3.4 mmol) 2,2,6,6-tetramethylpyperidine in 8 ml of tetrahydrofuran under a nitrogen atmosphere at −70° C., warmed to −50° C., and stirred for 20 minutes. After cooling to −70° C. again, the mixture was added with a solution of 0.44 g (1.5 mmol) of 1-ethoxymethy-6-phenylthio-2-thiouracil in 4 ml tetrahydrofuran dropwise over 15 minutes, stirred for an hour, added with 1.2 ml (15 mmol) ethyl iodide and stirred for 19 hours. Then, the mixture was added with 1 ml acetic acid, brought to room temperature, added with 30 ml ethyl acetate, washed with water and saturated aqueous solution of sodium chloride, dried on magnesium sulfate and concentrated under reused pressure. The residue was purified by silica gel chromatography (ethyl acetate/hexane=3:17) and crystallized from ethyl acetate to obtain 96 mg of the title compound (Yield: 20%).

EXAMPLE 38

Compound No. 359 was prepared in the same way as Example 37 by using 3,3',5,5'-tetramethyldiphenyl disulfide in place of diphenyl disulfide.

EXAMPLE 39

Compound No. 360 was prepared in the same way as Example 35 by using benzyl chloromethyl ether in place of chloromethyl ethyl ether.

EXAMPLE 40

Compound No. 361 was prepared in the same way as Example 35 by using benzyl chloromethyl ether and 3,3',5,5'-tetramethyldiphenyl disulfide respectively in place of chloromethyl ethyl ether and diphenyl disulfide.

EXAMPLE 41

Compound No 362 was prepared in the same way as Example 35 by using thymine and benzyl chloromethyl ether in place of 5-ethyluracil and chloromethyl ethyl ether.

EXAMPLE 42

Compound No. 41 was prepared in the same way as Example 22 by using chloromethyl propyl ether in place of chloromethyl methyl ether.

EXAMPLE 43

Compound No. 485 was prepared in the same way as Example 22 by using butyl chloromethyl ether in place of chloromethyl methyl ether.

EXAMPLE 44

Compound No. 365 was prepared in the same way as Example 35 by using 3,3',5,5'-tetrachlorodiphenyl disulfide in place of diphenyl disulfide.

EXAMPLE 45

Compound No. 366 was prepared in the same way as Example 35 by using 5-ethyl-2-thiouracil and 3,3',5,5'-tetrachlorodiphenyl disulfide respectively in place of 5-ethyluracil and diphenyl disulfide.

EXAMPLE 46

Compound No. 496 was prepared in the same way as Example 35 by using 5-isopropyluracil in place of 5-ethyluracil.

EXAMPLE 47

Compound No. 497 was prepared in the same way as Example 35 by using 5-isopropyl-2-thiouracil in place of 5-ethyluracil.

EXAMPLE 48

Compound No. 574 was prepared in the same way as Example 35 by using 5-cyclopropyluracil in place of 5-ethyluracil.

EXAMPLE 49

Compound No. 575 was prepared in the same way as Example 35 by using 5-cyclopropyl-2-thiouracil in place of 5-ethyluracil.

EXAMPLE 50

Compound No. 675 was prepared in the same way as Example 35 by using chloromethyl isopropyl other in place of chloromethyl ethyl ether.

EXAMPLE 51

Compound No. 675 was prepared in the same way as Example 35 by using 5-ethyl-2-thiouracil and chloromethyl isopropyl ether respectively in place of 5-ethyluracil and chloromethyl ethyl ether.

EXAMPLE 52

Compound No. 685 was prepared in the same way as Example 35 by using chloromethyl cyclohexyl ether in place of chloromethyl ethyl ether.

EXAMPLE 53

Compound No. 686 was prepared in the same way as Example 35 by using 5-ethyl-2-thiouracil and chloromethyl cyclohexyl ether respectively in place of 5-ethyluracil and chloromethyl ethyl ether.

EXAMPLE 54

Compound No. 689 was prepared in the same way as Example 35 by using chloromethyl cyclohexylmethyl ether in place of chloromethyl ethyl ether.

EXAMPLE 55

Compound No. 690 was prepared in the same way as Example 35 by using 5-ethyl-2-thiouracil and chloromethyl cyclohexylmethyl ether respectively in place of 5-ethyluracil and chloromethyl ethyl ether.

EXAMPLE 56

Compound No. 512 was prepared in the same way as Example 35 by using 5-isopropyluracil and benzyl chloromethyl ether respectively in place of 5-ethyluracil and chloromethyl ethyl ether.

EXAMPLE 57

Compound No. 513 was prepared in the same way as Example 35 by using 5-isopropyl-2-thiouracil and benzyl chloromethyl ether respectively in place of 5-ethyluracil and chloromethyl ethyl ether.

EXAMPLE 58

Compound No. 748 was prepared in the same way as Example 35 by using chloromethyl phenetyl ether in place of chloromethyl ethyl ether.

EXAMPLE 59

Compound No. 749 was prepared in the same way as Example 35 by using 5-ethyl-2-thioracil and chloromethyl phenetyl ether respectively in place of 5-ethyluracil and chloromethyl ethyl ether.

EXAMPLE 60

Compound No. 372 was prepared in the same way as Example 35 by using 5-ethyl-2-thiouracil and chloromethyl 4-methylbenzyl ether respectively in place of 5-ethyluracil and chloromethyl ethyl ether.

EXAMPLE 61

Compound No. 704 was prepared in the same way as Example 35 by using 5-ethyl-2-thiouracil and 4-chlorobenzyl chloromethyl ether respectively in place of 5-ethyluracil and chloromethyl ethyl ether.

EXAMPLE 62

Preparation of 6-benzyl-1-ethoxymethyl-5-ethyluracil (Compound No. 472)

To 100 ml of methylene chloride, 5.1 g (40 mmol) of 5-ethyluracil and 22 ml (88 mmol) of bistrimethylsilylacetamide were added under a nitrogen atmosphere and stirred for 40 minutes at room temperature. To this mixture, 4.1 ml (88 mmole) of chloromethyl ethyl ether and 0.15 g (0.4 mmol) of tetrabutylammonium iodide were added and heated under reflux for 15 hours. Then, the reaction mixture was poured into 50 ml of saturated sodium bicarbonate solution carefully and filtered through Celite. The organic layer was washed with water, dried on magnesium sulfate and concentrated under reduced pressure. The residue was crystallized from ethyl acetate to obtain 6.4 g of 1-ethoxymethyl-5-ethyluracil (Yield: 81%).

Then, 2.2 ml (4.4 mmol) of lithium diisopropylamide solution in tetrahydrofuran (2.1M) was added to 6 ml of tetrahydrofuran under a nitrogen atmosphere at −70° C., to which a solution of 0.40 g (2.0 mmol) of 1-ethoxymethyl-5-ethyluracil in 3 ml of tetrahydrofuran was added dropwise over 15 minutes. After stirring for 1 hour at −70° C., the reaction mixture was added with a solution of 0.27 g (2.6 mmol) of benzaldehyde in 2 ml of tetrahydrofuran dropwise over 10 minutes and allowed to react for 30 minutes. The reaction mixture was added with 1 ml of acetic acid, brought to room temperature and then added with 30 ml of ethyl acetate. The mixture was washed with water (3 ml ×5) and saturated aqueous solution of sodium hydrogencarbonate (twice), dried on magnesium sulfate and concentrated under reduced pressure.

The residue was dissolved in 10 ml of ethanol, added with 20 mg of 20% palladium hydroxide/carbon and stirred under a hydrogen atmosphere for a day at 55° C. Then, after removing the catalyst by filtration, the reaction mixture was concentrated. The residue was crystallized from hexane to obtain 0.28 g of 6 -benzyl-1-ethoxymethyl-5-ethyluracil (Yield: 85%).

EXAMPLE 63

Compound No. 474 was prepared in the same way as Example 62 by using 3,5-dimethylbenzaldehyde in place of benzaldehyde.

EXAMPLE 64

Preparation of 1-butyl-5-ethyl-6-phenylthiouracil (compound No. 252)

To a solution of 5.6 g (40 mmol) of 5-ethyluracil in 60 ml of dimethylformamide, 5.5 g (40 mmol) of potassium carbonate and 2.3 ml (20 mmol) of n-iodobutane were added and stirred for 2 hours at 120° C. The reaction mixture was concentrated under reduced pressure and distributed between dichloromethane and aqueous solution of ammonium chloride, and the organic layer was concentrated under reduced pressure. The residue was adsorbed on a silica gel column and eluted with 30% ethyl acetate/hexane to obtain 2.7 g of 1-butyl-5-ethyluracil (Yield: 69%).

Then, a solution of 4.4 mmol of lithium diisopropylamide in 2.8 ml of tetrahydrofuran was added dropwise to a solution of 392 mg (2.0 mmol) 1-butyl-5-ethyluracil in 9 ml of tetrahydrofuran under a nitrogen atmosphere at −70° C. and stirred for 70 minutes at −70° C. and further 5 minutes at −25° C. The mixture was cooled to −70° C. again, added with a solution of 567 mg (2.6 mmol) diphenyl disulfide in 3 ml of tetrahydrofuran, stirred for 20 minutes, added with 1 ml of acetic acid, brought to room temperature, washed with saturated aqueous solution of sodium chloride and concentrated under reduced pressure. The residue was adsorbed on a silica gel, eluted with 10% ethyl acetate/hexane and crystallized from hexane to obtain 40 mg of 1-butyl-5-ethyl-6-phenylthiouracil (Yield: 7%).

EXAMPLE 65

Compound No. 363 was prepared in the same way as Example 35 by using 5-ethyl-2-thiouracil and benzyl chloromethyl ether respectively in place of 5-ethyluracil and chloromethyl ethyl ether.

EXAMPLE 66

Compound No. 364 was prepared in the same way as Example 35 by using 5-ethyl-2-thiouracil, benzyl chloromethyl ether and 3,3',5,5'-tetramethyldiphenyl disulfide respectively in place of 5-ethyluracil, chloromethyl ethyl ether and diphenyl disulfide.

EXAMPLE 67

Preparation of 5-(2-(E)-bromovinyl)-1-(ethoxymethyl)-6-(phenylthio) uracil (Compound No. 270)

In 50 ml of dichloromethane, 4.76 g (20 mmol) of 5-iodouracil was suspended and added with 11 ml (45 mmol) of bistrimethylsilylacetamide and stirred for 15 minutes at room temperature to form a homogeneous solution. This solution was added with 2.04 ml (22 mmol) of chloromethyl ethyl ether and 60 mg of tetra-n-butylammonium iodide and heated under reflux for 3 hours. After the solvent was evaporated under reduced pressure, the residue was added with water to produce crystals, which were taken by filtration. The crystals were washed by suspending them in hot methanol and recovering them by cooling and filtration to obtain 5.43 g of 1-(ethoxy-methyl)-5-iodouracil.

Then, 1.184 g (4 mmol) of 1-(ethoxymethyl)-5-iodouracil, 870 μg (8 mmol) of ethyl acrylate, 45 mg of palladium acetate and 0.6 ml of triethylamine were dissolved in 40 ml of dimethylformamide, heated and stirred for 5 hours at 70° C. After the solvent was evaporated under reduced pressure, the residue was adsorbed on a silica gel column, eluted with a solution of dichloromethan/ethyl acetate (1:1 v/v) to recover the desired fraction, from which the solvent was evaporated under reduced pressure to obtain 798 mg of 5-(2-(E)-carboethoxyvinyl)-1-(ethoxymethyl) uracil as crystals.

Then, 0.16 g (4.0 mmol) of sodium hydroxide and 0.54 g (2.0 mmol) of 5-(2- (E) -carboethoxyvinyl) -1-(ethoxymethyl) -uracil were added to 8 ml of water, stirred for 4.5 hours, neutralized with 1N hydrochloric acid and added with 10 ml of dimethylformamide to obtain a homogeneous solution.

This solution was then added with 0.62 g (4.5 mmol) of potassium carbonate, stirred for 5 minutes at room temperature to make it a homogeneous solution, then added with 0.36 g (2.0 mmol) of N-bromosuccinimide and stirred for 30 minutes. The reaction mixture was concentrated under reduced pressure and distributed between chloroform and aqueous solution of ammonium chloride, and the organic layer was concentrated under reduced pressure. The residue was adsorbed on a silica gel column and eluted with 20% ethyl acetate/hexane to collect the desired fraction, from which the solvent was evaporated under reduced pressure to obtain 0.15 g of 5-(2-(E)-bromovinyl)-1-(ethoxymethyl) uracil (Yield: 28%).

Then, a solution of 0.15 g (0.56 mmol) 5-(2-(E)-bromovinyl) -1-ethoxymethyl)uracil in 1.7 ml of tetrahydrofuran was added dropwise to a solution of 1.22 mmol of lithium diisopropylamide in 2.3 ml of tetrahydrofuran under a nitrogen atmosphere at −70° C. over 7 minutes and stirred for 40 minutes, added with a solution of 0.16 g (0.73 mmol) diphenyl disulfide in 1 ml of tetrahydrofuran and stirred for 1 hour. The reaction mixture was washed with saturated aqueous solution of sodium chloride and concentrated under reduced pressure. The residue was absorbed on a silica gel column, eluted with 15% ethyl acetate/hexane to collect the desired faction, from which the solvent was evaporated under reduced pressure to obtain 11 mg of the target compound (Yield: 5%. m.p.: 143°–148° C.).

Compounds No. 35 to 40, 42 to 246, 248 to 251, 253 to 269, 271 to 356, 367 to 371, 373 to 471, 473, 475 to 484, 486 to 495, 498 to 511, 514 to 573, 576 to 674, 677 to 684, 687, 688, 691 to 703, 705 to 747 and 750 to 803 in Table 1 may be prepared similarly according to the methods described in the working examples above.

EXAMPLE 68

Production of tablet

| | |
|---|---|
| 1-[(2-acetoxyethoxy)methyl]-6-phenylthiothymine | 10 g |
| Corn starch | 65 g |
| Carboxycellulose | 20 g |
| Polyvinyl pyrrolidone | 3 g |
| Calcium stearate | 2 g |
| Total weight | 100 g |

The above-mentioned components were well mixed and tablets were produced by a direct tableting method. Each tablet had a weight of 100 mg and contained 10 mg of [1-](2-acetoxyethoxy)methyl]-6-phenylthiothymine] *1-[(2-acetoxyethoxy)methyl]-6-phenylthiothymine.*

EXAMPLE 69

Production of powder and encapsulated medicine

| | |
|---|---|
| 1-[2-acetoxyethoxy)methyl]-6-phenylthiothymine | 20 g |
| Crystalline cellulose | 80 g |
| Total weight | 100 g |

Both powder components were well mixed to obtain a powder formulation. 100 mg of the thus-obtained powder was charged into a hard capsule of No. 5 to obtain an encapsulated medicine.

EXAMPLE 70

Inhibitory activity for HIV infection

In RPMI 1640 DM culture medium containing 20 mM of Hepes buffer solution, 10% fetal bovine serum and 20 μg/ml of gentamycin, $3\times10^4$ MT-4 cells (human T cell clone which is destroyed by the infection of HIV) were infected with HIV in an amount of 100 times as large as expected to cause 50% infection of the cells. Immediately thereafter, a predetermined amount of sample was added to the culture medium using 50 mg/ml sample solutions in dimethyl sulfoxide and the cells were cultured at 37° C.

After 5 days of incubation, the number of existing cells was counted to determine the concentration of the compound for preventing the death of 50% of the MT-4 cells. Separately, MT-4 cells were cultured in the same way as above except that they were not infected with HIV to determine the concentration of the compound at which 50% of the MT-4 cells were destroyed.

Both results are shown in Table 2.

TABLE 2

| Compound No. | 50% inhibitory concentration of HIV infection (μM) | 50% cytotoxic concentration to MT-4 cells (μM) |
|---|---|---|
| 1 | 2.8 | 196 |
| 2 | 6.7 | 314 |
| 3 | <0.8 | 236 |
| 4 | <0.8 | 240 |
| 5 | 1.8 | 218 |
| 7 | 7.1 | 292 |
| 8 | 9.9 | 218 |
| 10 | 11 | 162 |
| 11 | 7.5 | 78 |
| 12 | 7.6 | 53 |
| 13 | 11 | 170 |
| 14 | 12 | 66 |
| 16 | 21 | 420 |
| 17 | 0.96 | 171 |
| 20 | 8.6 | 292 |
| 22 | 2.1 | 244 |
| 23 | <0.8 | 215 |
| 24 | 5.7 | 169 |
| 25 | 1.1 | 191 |
| 26 | 1.7 | 193 |
| 29 | 4.3 | 96 |
| 30 | 1.2 | 89 |
| 31 | 13 | 249 |
| 32 | 1.2 | 154 |
| 41 | 5.6 | 147 |
| 247 | 0.016 | 123 |
| 252 | 0.016 | 45 |
| 357 | 0.005 | >100 |
| 358 | 0.026 | 81 |
| 359 | 0.004 | >100 |
| 360 | 0.0025 | 30 |
| 361 | 0.005 | >20 |
| 362 | 0.076 | 133 |
| 363 | 0.0078 | >10 |
| 364 | 0.0069 | >20 |
| 365 | 0.0074 | 45 |
| 366 | 0.013 | 45 |
| 372 | 0.012 | >20 |
| 472 | 0.041 | 245 |
| 474 | 0.0064 | >500 |
| 485 | 4.7 | 83 |
| 496 | 0.012 | 106 |
| 497 | 0.014 | >100 |
| 512 | 0.0027 | >20 |
| 513 | 0.0068 | >20 |
| 574 | 0.10 | 223 |
| 575 | 0.095 | 46 |
| 675 | 0.34 | 143 |
| 676 | 0.22 | >100 |
| 685 | 3.8 | >100 |
| 686 | 1.6 | 223 |
| 689 | 0.45 | 17 |
| 690 | 0.35 | >100 |
| 704 | 0.012 | 20 |
| 748 | 0.096 | 38 |
| 749 | 0.091 | >20 |

What is claimed is:

1. A pyrimidine derivative represented by the following formula (I):

[I]

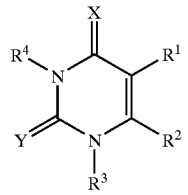

wherein $R^1$ represents $C_1$ to $C_5$ alkyl; $C_3$ to $C_8$ cycloalkyl; $C_2$ to $C_5$ alkenyl optionally substituted by one or more substituents selected from the group consisting of a halogen atom, phenyl, cyano, $C_2$to $C_6$ alkoxycarbonyl and carbamoyl groups; $C_2$ to $C_5$ alkynyl optionally substituted by one or more substituents selected from the group consisting of a halogen atom, phenyl, cyano, $C_2$ to $C_6$ alkoxycarbonyl and carbamoyl groups; $C_2$ to $C_5$ alkylcarbonyl optionally substituted by one or more substituents selected from the group consisting of a halogen atom, phenyl, cyano, $C_2$ to $C_6$ alkoxycarbonyl and carbamoyl groups; $C_7$ to $C_{13}$ arylcarbonyl optionally substituted by one or more substituents selected from the group consisting of a halogen atom, phenyl, cyano, $C_2$ to $C_6$ alkoxycarbonyl and carbamoyl groups; $C_8$ to $C_{14}$ arylcarbonylalkyl optionally substituted by one or more substituents selected from the group consisting of a halogen atom, phenyl, cyano, $C_2$ to $C_6$ alkoxycarbonyl and carbamoyl groups; $C_6$ to $C_{12}$ arylthio optionally substituted by one or more substituents selected from the group consisting of a halogen atom, phenyl, cyano, $C_2$ to $C_6$ alkoxycarbonyl and carbamoyl groups; $C_7$ to $C_{13}$ arylcarbonyl optionally substituted by one or more substituents selected from the group consisting of a halogen atom, phenyl, cyano, $C_2$ to $C_6$ alkoxycarbonyl and carbamoyl groups; $C_8$ to $C_{14}$ arylcarbonylalkyl optionally substituted by one or more substituents selected from the group consisting of a halogen atom, phenyl, cyano, $C_2$ to $C_6$ alkoxycarbonyl and carbamoyl groups; $C_6$ to $C_{12}$ arylthio optionally substituted by one or more substituents selected from the group consisting of a halogen atom, phenyl, cyano, $C_2$ to $C_6$ alkoxycarbonyl and carbamoyl groups; or $C_7$ to $C_{17}$ aralkyl group optionally substituted by one or more substituents selected from the group consisting of a halogen atom, phenyl, cyano, $C_2$ to $C_6$ alkoxycarbonyl and carbamoyl groups, $R^2$ represents $C_6$ to $C_{10}$ arylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano, and $C_2$ to $C_7$ acyl groups; $C_1$ to $C_5$ alkylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_3$ to $C_{10}$ cycloalkylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_6$ to $C_{12}$ arylsulfinyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_1$ to $C_5$ alkylsulfinyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_3$ to $C_{10}$ cycloalkylsulfinyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_2$ to $C_5$ alkenyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_2$ to $C_5$ alkynyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_7$ to $C_{11}$ aralkyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_7$ to $C_{13}$ arylcarbonyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_8$ to $C_{14}$ arylcarbonylalkyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; or $C_6$ to $C_{12}$ aryloxy group optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ and $C_7$ acyl groups;

$R^3$ represents ethyl; $C_3$ to $C_{10}$ branched alkyl; or —$CH_2$—$Z(CH_2)_n$—$R^5$ group where $R^5$ represents a hydrogen atom; halogen atom; hydroxyl; nicotinoyloxy; formyloxy; $C_2$ to $C_{11}$ alkylcarbonyloxy; $C_4$ to $C_{11}$ cycloalkylcarbonyloxy; $C_8$ to $C_{12}$ aralkylcarbonyloxy; $C_7$ to $C_{13}$ arylcarbonyloxy; azido; $C_2$ to $C_{11}$ alkoxycarbonyloxy optionally substituted by one or more substituents selected from the group consisting of a halogen atom, $C_6$ to $C_{12}$ aryl, $C_1$ to $C_5$ alkoxy and $C_1$ to $C_5$ halogenated alkyl groups; $C_2$ to $C_{11}$ N-alkylcarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_7$ to $C_{13}$ N-arylcarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_2$ to $C_{11}$ N-alkylthiocarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_7$ to $C_{13}$ N-arylthiocarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_1$ to $C_{10}$ alkoxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_7$ to $C_{13}$ aralkyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_3$ to $C_{10}$ branched alkyl optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_3$ to $C_{10}$ cycloalkyl optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; or $C_6$ to $C_{12}$ aryl group optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups, Z represents an oxygen atom, sulfur atom or methylene group, and n represents 0 or an integer of 1 to 5, $R^4$ represents a hydrogen atom;

X and Y independently represent an oxygen or sulfur atom; provided that when $R^4$ represents a hydrogen atom and Z represents an oxygen atom or methylene group, $R^5$ does not represent hydroxyl group, or a pharmaceutically acceptable salt thereof.

2. A pyrimidine derivative represented by the following formula (I'):

[I']

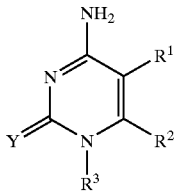

wherein:

$R^1$ represents $C_1$ to $C_5$ alkyl; $C_3$ to $C_8$ cycloalkyl; $C_2$ to $C_5$ alkenyl optionally substituted by one or more substituents selected from the group consisting of a halogen atom, phenyl, cyano, $C_2$ to $C_6$ alkoxycarbonyl and carbamoyl groups; $C_2$ to $C_5$ alkynyl optionally substituted by one or more substituents selected from the group consisting of a halogen atom, phenyl, cyano, $C_2$ to $C_6$ alkoxycarbonyl and carbamoyl groups; $C_2$ to $C_5$ alkylcarbonyl optionally substituted by one or more substituents selected from the group consisting of a halogen atom, phenyl, cyano, $C_2$ to $C_6$ alkoxycarbonyl and carbamoyl groups; $C_7$ to $C_{13}$ arylcarbonyl optionally substituted by one or more substituents selected from the group consisting of a halogen atom, phenyl, cyano, $C_2$ to $C_6$ alkoxycarbonyl and carbamoyl groups; $C_8$ to $C_{14}$ arylcarbonylalkyl optionally substituted by one or more substituents selected from the group consisting of a halogen atom, phenyl, cyano, $C_2$ to $C_6$ alkoxycarbonyl and carbamoyl groups; $C_6$ to $C_{12}$ arylthio optionally substituted by one or more substituents selected from the group consisting of a halogen atom, phenyl, cyano, $C_2$ to $C_6$ alkoxycarbonyl and carbamoyl groups; or $C_7$ to $C_{17}$ aralkyl group optionally substituted by one or more substituents selected from the group consisting of a halogen atom, phenyl, cyano, $C_2$ to $C_6$ alkoxycarbonyl and carbamoyl groups, $R^2$ represents $C_6$ to $C_{10}$ arylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano, and $C_2$ to $C_7$ acyl groups; $C_1$ to $C_5$ alkylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_3$ to $C_{10}$ cycloalkylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_6$ to $C_{12}$ arylsulfinyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_1$ to $C_5$ alkylsulfinyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_3$ to $C_{10}$ cycloalkylsulfinyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_2$ to $C_5$ alkenyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_2$ to $C_5$ alkynyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_7$ to $C_{11}$ aralkyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_7$ to $C_{13}$ arylcarbonyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_8$ to $C_{14}$ arylcarbonylalkyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; or $C_6$ to $C_{12}$ aryloxy group optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups;

$R^3$ represents ethyl; $C_3$ to $C_{10}$ branched alkyl; or —$CH_2$—$Z(CH_2)_n$—$R^5$ group where $R^5$ represents a hydrogen atom; halogen atom; hydroxyl; nicotinoyloxy; formyloxy; $C_2$ to $C_{11}$ alkylcarbonyloxy; $C_4$ to $C_{11}$ cycloalkylcarbonyloxy; $C_8$ to $C_{12}$ aralkylcarbonyloxy; $C_7$ to $C_{13}$ arylcarbonyloxy; azido; $C_2$ to $C_{11}$ alkoxycarbonyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_2$ to $C_{11}$ N-alkylcarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_7$ to $C_{13}$ N-arylcarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_2$ to $C_{11}$ N-alkylthiocarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_7$ to $C_{13}$ N-arylthiocarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_1$ to $C_{10}$ alkoxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_7$ to $C_{13}$ aralkyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_3$ to $C_{10}$ branched alkyl optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_3$ to $C_{10}$ cycloalkyl optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; or $C_6$ to $C_{12}$ aryl group optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups, Z represents an oxygen atom, sulfur atom or methylene group, and n represents 0 or an integer of 1 to 5, and Y represents an oxygen or sulfur atom, or a pharmaceutically acceptable salt thereof.

3. A [compounds] *pyrimidine derivative* according to claim 1 or 2, wherein:

$R^1$ represents $C_1$ to $C_5$ alkyl; $C_3$ to $C_8$ cycloalkyl; $C_2$ to $C_5$ alkenyl optionally substituted by one or more substituents selected from the group consisting of a halogen atom, phenyl, cyano, $C_2$ to $C_6$ alkoxycarbonyl and carbamoyl groups; $C_2$ to $C_5$ alkynyl optionally substituted by one or more substituents selected from the group consisting of a halogen atom, phenyl, cyano, $C_2$ to $C_6$ alkoxycarbonyl and carbamoyl groups; $C_2$ to $C_5$ alkylcarbonyl; $C_7$ to $C_{13}$ arylcarbonyl; $C_9$ to $C_{14}$ arylcarbonylalkyl; $C_6$ to $C_{12}$ arylthio; or $C_7$ to $C_{17}$ aralkyl group, $R^2$ represents $C_6$ to $C_{10}$ arylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_1$ to $C_5$ alkylthio; $C_3$ to $C_{10}$ cycloalkylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_6$ to $C_{12}$ arylsulfinyl; $C_1$ to $C_5$ arylsulfinyl; $C_3$ to $C_{10}$ cycloalkylsulfinyl; $C_2$ to $C_5$ alkenyl; $C_2$ to $C_5$ alkynyl; $C_7$ to $C_{11}$ aralkyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_7$ to $C_{13}$ arylcarbonyl; $C_8$ to $C_{14}$ arylcarbonylalkyl; or $C_6$ to $C_{12}$ aryloxy, $R^3$ represents ethyl; or $—CH_2—Z—(CH_2)_n—R^5$ group where $R^5$ represents a hydrogen atom; halogen atom; hydroxyl; nicotinoyloxy; formyloxy; $C_2$ to $C_{11}$ alkylcarbonyloxy; $C_4$ to $C_{11}$ cycloalkylcarbonyloxy; $C_8$ to $C_{12}$ aralkylcarbonyloxy; $C_7$ to $C_{13}$ arylcarbonyloxy; azido; $C_2$ to $C_{11}$ alkoxycarbonyloxy; $C_2$ to $C_8$ N-alkylcarbamoyloxy; $C_7$ to $C_{13}$ N-arylcarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_2$ to $C_8$ N-alkylthiocarbamoyloxy; $C_7$ to $C_{13}$ N-arylthiocarbamoyloxy optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_1$ to $C_{10}$ alkoxy; $C_7$ to $C_{13}$ aralkyloxy optionally substituted by one or more substituents selected by the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups; $C_3$ to $C_5$ branched alkyl; $C_5$ to $C_7$ cycloalkyl; or $C_6$ to $C_{12}$ aryl group optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups, Z represents an oxygen atom, sulfur atom or methylene group, and n represents 0 or an integer of 1 to 5;

*or a pharmaceutically acceptable salt thereof.*

4. A [compound] *pyrimidine derivative* according to claim 3, wherein:

$R^1$ represents $C_1$ to $C_5$ alkyl; $C_3$ to $C_8$ cycloalkyl; or $C_2$ to $C_5$ alkenyl optionally substituted by one or more substituents selected from the group consisting of a halogen atom, phenyl, cyano, $C_2$ to $C_6$ alkoxycarbonyl and carbamoyl groups, $R^2$ represents $C_6$ to $C_{10}$ arylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; $C_3$ to $C_{10}$ cycloalkylthio optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups; or $C_7$ to $C_{11}$ aralkyl optionally substituted by one or more substituents selected from the group consisting of a halogen atom, $C_1$ to $C_5$ alkyl, $C_1$ to $C_5$ halogenated alkyl, $C_1$ to $C_5$ alkoxy, phenyl, hydroxyl, nitro, amino, cyano and $C_2$ to $C_7$ acyl groups, $R^3$ represents ethyl; or $—CH_2—Z—(CH_2)_n—R^5$ group where $R^5$ represents a hydrogen atom; halogen atom; hydroxyl; nicotinoyloxy; formyloxy; $C_2$ to $C_{11}$ alkylcarbonyloxy; $C_4$ to $C_{11}$ cycloalkylcarbonyloxy; $C_8$ to $C_{12}$ aralkylcarbonyloxy; $C_7$ to $C_{13}$ arylcarbonyloxy; azido; $C_2$ to $C_{11}$ alkoxycarbonyloxy; $C_2$ to $C_8$ N-alkylcarbamoyloxy; $C_7$ to $C_{13}$ N-arylcarbamoyloxy; $C_2$ to $C_8$ N-alkylthiocarbamoyloxy; $C_7$ to $C_{13}$ N-arylthiocarbamoyloxy; $C_1$ to $C_{10}$ alkoxy; $C_7$ to $C_{13}$ aralkyloxy; $C_3$ to $C_5$ branched alkyl; $C_5$ to $C_7$ cycloalkyl; or $C_6$ to $C_{12}$ aryl group optionally substituted by one or more substituents selected from the group consisting of a halogen atom, $C_6$ to $C_{12}$ aryl, $C_1$ to $C_5$ alkyl, $C_1$ to $C_5$ alkoxy and $C_1$ to $C_5$ halogenated alkyl groups, Z represents an oxygen, sulfur or methylene group, and n represents 0 or an integer of 1 to 5;

*or a pharmaceutically acceptable salt thereof.*

5. A [compound] *pyrimidine derivative* according to claim 4, wherein:

$R^1$ represents $C_1$ to $C_5$ alkyl, $R^2$ represents a phenylthio group optionally substituted by a $C_1$ to $C_3$ alkyl or halogen atom; or a benzyl group optionally substituted by a $C_1$ to $C_3$ alkyl or halogen atom, $R^3$ represents a $—CH_2—Z—(CH_2)_n—R^5$ group where $R^5$ represents a hydrogen atom; or a phenyl group optionally substituted by a $_1$ to $_3$ alkyl or a halogen atom, Z represents an oxygen atom, and n represents an integer of 1 to 3, $R^4$ represents a hydrogen atom, X represents an oxygen atom, and Y represents an oxygen atom or sulfur atom;

*or a pharmaceutically acceptable salt thereof.*

6. A [compound] *pyrimidine derivative* according to claim 5, wherein:

$R^1$ represents a*n* ethyl or isopropyl group, $R^2$ represents a phenylthio group optionally substituted by a $C_1$ to $C_3$ alkyl or halogen atom;

$R^3$ represents a $—CH_2—Z—(CH_2)_n—R^5$ group where $R^5$ represents a hydrogen atom; Z represents an oxygen atom, and n represents an integer of 1 to 3, $R^4$ represents a hydrogen atom, X represents an oxygen atom, and Y represents an oxygen or sulfur atom;

*or a pharmaceutically acceptable salt thereof.*

7. A [compound] *pyrimidine derivative* according to claim [6] *5*, wherein:

$R^1$ represents an ethyl or isopropyl group, $R^2$ represents a benzyl group optionally substituted by a a $C_1$ to $C_3$ alkyl or halogen atom, $R^3$ represents a $—CH_2—Z—(CH_2)_n—R^5$ group where $R^5$ represents a hydrogen atom; Z represents an oxygen atom, and n represents an integer of 1 to 3, $R^4$ represents a hydrogen atom, X represents an oxygen atom, and Y represents an oxygen or sulfur atom;

*or a pharmaceutically acceptable salt thereof.*

8. A pharmaceutical composition containing a [6-substituted acyclopyrimidine nucleoside] *pyrimidine* derivative or a pharmaceutically acceptable salt thereof according to [any one of claims 1–7] *claim 1,* in admixture with a pharmaceutical vehicle.

9. A pharmaceutical composition according to claim 8, which has effective antiviral activity.

10. A pharmaceutical composition according to claim 8, which has effective antiretroviral activity.

11. The pharmaceutical composition of claim 8, which is used to treat a [vital] *viral* infection which is susceptible to treatment.

*12. A pyrimidine derivative having the following structure:*

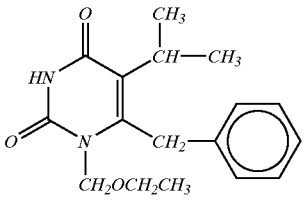

*or a pharmaceutically acceptable salt thereof.*

*13. A pharmaceutical composition containing the pyrimidine derivative of claim 12 in combination with a pharmaceutically acceptable carrier.*

*14. A method of treating an HIV infection in a host, comprising administering to the host an effective treatment amount of the pyrimidine derivative of claim 12.*

*15. A pharmaceutical composition containing a pyrimidine derivative or a pharmaceutically acceptable salt thereof according to claim 2, in admixture with a pharmaceutical vehicle.*

* * * * *